US012758172B2

(12) United States Patent
So et al.

(10) Patent No.: US 12,758,172 B2
(45) Date of Patent: *Oct. 13, 2026

(54) DYNAMIC ANGIOGRAPHIC IMAGING

(71) Applicant: LONDON HEALTH SCIENCES CENTRE RESEARCH INC., London (CA)

(72) Inventors: Aaron So, Mississauga (CA); Ting-Yim Lee, London (CA)

(73) Assignee: London Health Sciences Centre Research Inc., London (CA)

( * ) Notice: Subject to any disclaimer, the term of this patent is extended or adjusted under 35 U.S.C. 154(b) by 0 days.

This patent is subject to a terminal disclaimer.

(21) Appl. No.: 18/765,142

(22) Filed: Jul. 5, 2024

(65) Prior Publication Data

US 2024/0358338 A1 Oct. 31, 2024

Related U.S. Application Data

(63) Continuation of application No. 17/055,784, filed as application No. PCT/CA2019/050668 on May 16, 2019, now Pat. No. 12,059,283.

(Continued)

(51) Int. Cl.
*A61B 6/50* (2024.01)
*A61B 6/03* (2006.01)

(52) U.S. Cl.
CPC .............. *A61B 6/504* (2013.01); *A61B 6/032* (2013.01)

(58) Field of Classification Search
CPC ....... A61B 6/504; A61B 6/032; A61B 5/0263; A61B 5/0275; A61B 6/481; A61B 6/5217; G16H 20/40; G16H 30/20; G16H 30/40; G16H 50/30; G16H 50/50; G01R 33/56308; G01R 33/5635
See application file for complete search history.

(56) References Cited

U.S. PATENT DOCUMENTS

| | | | |
|---|---|---|---|
| 6,745,066 | B1 | 6/2004 | Lin et al. |
| 7,689,267 | B2 | 3/2010 | Prince |

(Continued)

FOREIGN PATENT DOCUMENTS

| | | | |
|---|---|---|---|
| CN | 104688259 A * | 6/2015 | |
| JP | 2015-126868 | 6/2015 | |

(Continued)

OTHER PUBLICATIONS

CN-104688259—machine translation (Year: 2018).*

(Continued)

*Primary Examiner* — Alexei Bykhovski
(74) *Attorney, Agent, or Firm* — Knobbe, Martens, Olson & Bear, LLP

(57) ABSTRACT

Described herein is a computer implemented method for dynamic angiographic imaging comprising: obtaining image data comprising a plurality of corresponding images capturing at least a portion of both an increase phase and a decline phase of a contrast agent in a blood vessel of interest; generating at least one time-enhancement curve of the contrast agent based on the image data; determining a blood flow characteristic in the blood vessel of interest based on the time-enhancement curve. Systems for implementing the method and computer readable media incorporating the method are also described.

21 Claims, 19 Drawing Sheets

Related U.S. Application Data

(60) Provisional application No. 62/672,896, filed on May 17, 2018.

(56) References Cited

U.S. PATENT DOCUMENTS

| | | | | |
|---|---|---|---|---|
| 8,792,701 | B2 | 7/2014 | Djeridane et al. | |
| 8,929,632 | B2 | 1/2015 | Horz et al. | |
| 9,174,065 | B2 * | 11/2015 | Gertner | A61N 5/062 |
| 9,433,392 | B2 | 9/2016 | Ohishi | |
| 2007/0167731 | A1 | 7/2007 | Taxt et al. | |
| 2008/0119715 | A1 * | 5/2008 | Gonzalez Molezzi | A61B 6/481 600/407 |
| 2011/0150309 | A1 | 6/2011 | Barfett et al. | |
| 2014/0114185 | A1 * | 4/2014 | Tolkowsky | A61B 6/504 600/431 |
| 2015/0087956 | A1 * | 3/2015 | Yao | A61B 6/022 600/407 |
| 2015/0221082 | A1 * | 8/2015 | Carmi | A61B 8/5223 382/128 |
| 2017/0007195 | A1 | 1/2017 | Molloi | |
| 2024/0331159 | A1 * | 10/2024 | So | G16H 50/30 |

FOREIGN PATENT DOCUMENTS

| | | | | |
|---|---|---|---|---|
| WO | WO 2005/044104 | A1 | 5/2005 | |
| WO | WO-2009009140 | A1 * | 1/2009 | A61B 5/029 |
| WO | WO 2010/045003 | A1 | 4/2010 | |

OTHER PUBLICATIONS

International Search Report and Written Opinion in PCT/CA2019/050668, issued Sep. 5, 2019.

Extended European Supplemental Search Report in European Patent Application No. 19803277.3, mailed Feb. 23, 2022.

Cook et al. (2017) "Diagnostic accuracy of computed tomography-derived fractional flow reserve. A systematic review" JAMA Cardiology; vol. 2(7): pp. 803-810.

Garcia et al. (2018) "Distribution of blood flow velocity in the normal aorta: Effect of age and gender" J Magn Reson Imaging; vol. 47(2): pp. 487-498.

Hubbard et al. (2018) "Comprehensive assessment of coronary artery disease by using first-pass analysis dynamic CT perfusion: validation in a swine model" Radiology; vol. 286(1): pp. 93-102.

Kim et al. (2010) "Patient-Specific Modeling of Blood Flow and Pressure in Human Coronary Arteries" Annals of Biomedical Engineering; vol. 38(10): pp. 3195-3209.

Kishi et al. (2018) "Fractional Flow Reserve Estimated at Coronary CT Angiography in Intermediate Lesions: Comparison of Diagnostic Accuracy of Different Methods to Determine Coronary Flow Distribution" Radiology; vol. 287(1): pp. 76-84.

Kojima et al. (2021) "New transluminal attenuation gradient derived from dynamic coronary CT angiography: diagnostic ability of ischemia detected by $^{13}$N-ammonia PET" Heart and Vessels; vol. 36: pp. 433-441.

Lantz et al. (2018) "Intracardiac Flow at 4D CT: Comparison with 4D Flow MRI" Radiology; vol. 289(1): pp. 51-58.

Lantz et al. (2019) "Impact of Pulmonary Venous Inflow on Cardiac Flow Simulations: Comparison with In Vivo 4D Flow MRI" Annals of Biomed Eng; vol. 47(2): pp. 413-424.

Nagao et al. (2016) "Quantification of coronary flow using dynamic angiography with320-detector row CT and motion coherence image processing: Detection of ischemia for intermediate coronary stenosis" Eur J Radiol; vol. 85: pp. 996-1003.

Nakanishi et al. (2016) "Noninvasive FFR derived from coronary CT angiography in the management of coronary artery disease: technology and clinical update" Vascular Health and Risk Management; vol. 12: pp. 269-278.

Petersson et al. (2016) "Retrospectively gated intracardiac 4D flow MRI using spiral trajectories" Magn Reson Med; vol. 75(1): pp. 196-206.

Precious et al. (2015) "Fractional Flow Reserve Modeled From Resting Coronary CT Angiography: State of the Science" American Journal of Roentgenology; vol. 204: pp. W243-W248.

Sharma et al. (2012) "A Framework for Personalization of Coronary Flow Computations During Rest and Hyperemia" 34th Annual International Conference of the IEEE Engineering in Medicine and Biology Society: pp. 6665-6668.

* cited by examiner g.

h.

DYNAMIC ANGIOGRAPHIC IMAGING

CROSS REFERENCE TO RELATED APPLICATIONS

This application is a continuation of U.S. application Ser. No. 17/055,784, filed Nov. 16, 2020, which is the U.S. national phase of International Application No. PCT/CA2019/050668, filed May 16, 2019, which claims benefit of U.S. Provisional Application No. 62/672,896, filed May 17, 2018, all of which are expressly incorporated by reference in their entireties.

BACKGROUND OF THE INVENTION

Field of the Invention

The present invention relates to dynamic imaging of flow, and more particularly to assessment of a blood vessel in a subject based on dynamic imaging of contrast agent flow through the blood vessel.

Description of the Related Art

The clinical gold standard for assessing the functional significance of a coronary artery stenosis is the invasive fractional flow reserve (FFR) technique, in which a specialized catheter is advanced to the culprit artery with aids of fluoroscopy to measure the flow pressure gradient across a plaque during maximal hyperemia. Recently, non-invasive assessment of FFR using CT coronary angiography (CCTA) images has emerged as a promising avenue for evaluation of higher risk patients requiring anatomical and functional assessment for coronary artery disease (CAD). However, at the present time, FFR evaluation by CCTA requires extensive post-processing and calculation (often greater than several hours) and, therefore, is not presently suitable for evaluation of patients in a medical emergency situation or setting. Furthermore, the DeFACTO and NXT trials reported that imaging based estimation of FFR demonstrated only moderate correlation (0.73) and diagnostic accuracy (~80%) compared to catheter-based FFR measurement. A recent systematic review has revealed that the accuracy of FFR-CT measurement decreases as the degree of stenosis increases when compared to the gold standard catheter-based FFR measurement (Cook et al. (2017) Diagnostic accuracy of computed tomography-derived fractional flow reserve. A systematic review. JAMA Cardiol; 2(7):803-810).

Accordingly, there is a continuing need for alternative methods and systems for imaging based assessment of a blood vessel in a subject.

SUMMARY OF THE INVENTION

In an aspect there is provided, a computer implemented method for dynamic angiographic imaging comprising:

- obtaining image data comprising a plurality of corresponding images capturing at least a portion of both an increase phase and a decline phase of a contrast agent in a blood vessel of interest;
- generating at least one time-enhancement curve of the contrast agent based on the image data, the time-enhancement curve having an upslope and a downslope;
- determining a blood flow characteristic in the blood vessel of interest based on the time-enhancement curve.

In another aspect there is provided, a system for dynamic angiographic imaging comprising:

- a memory for storing image data comprising a plurality of corresponding images capturing at least a portion of both an increase phase and a decline phase of a contrast agent in a blood vessel of interest;
- a processor configured to generate at least one time-enhancement curve of the contrast agent based on the image data, the time-enhancement curve having an upslope and a downslope; and to determine a blood flow characteristic in the blood vessel of interest based on the time-enhancement curve.

In a further aspect, a computer readable medium embodying a computer program for dynamic angiographic imaging is also provided.

DETAILED DESCRIPTION OF PREFERRED EMBODIMENTS

With reference to the drawings, a system and method for dynamic angiographic imaging (DAI) is described. The system and method compare favourably with current CCTA techniques.

Figure 1:
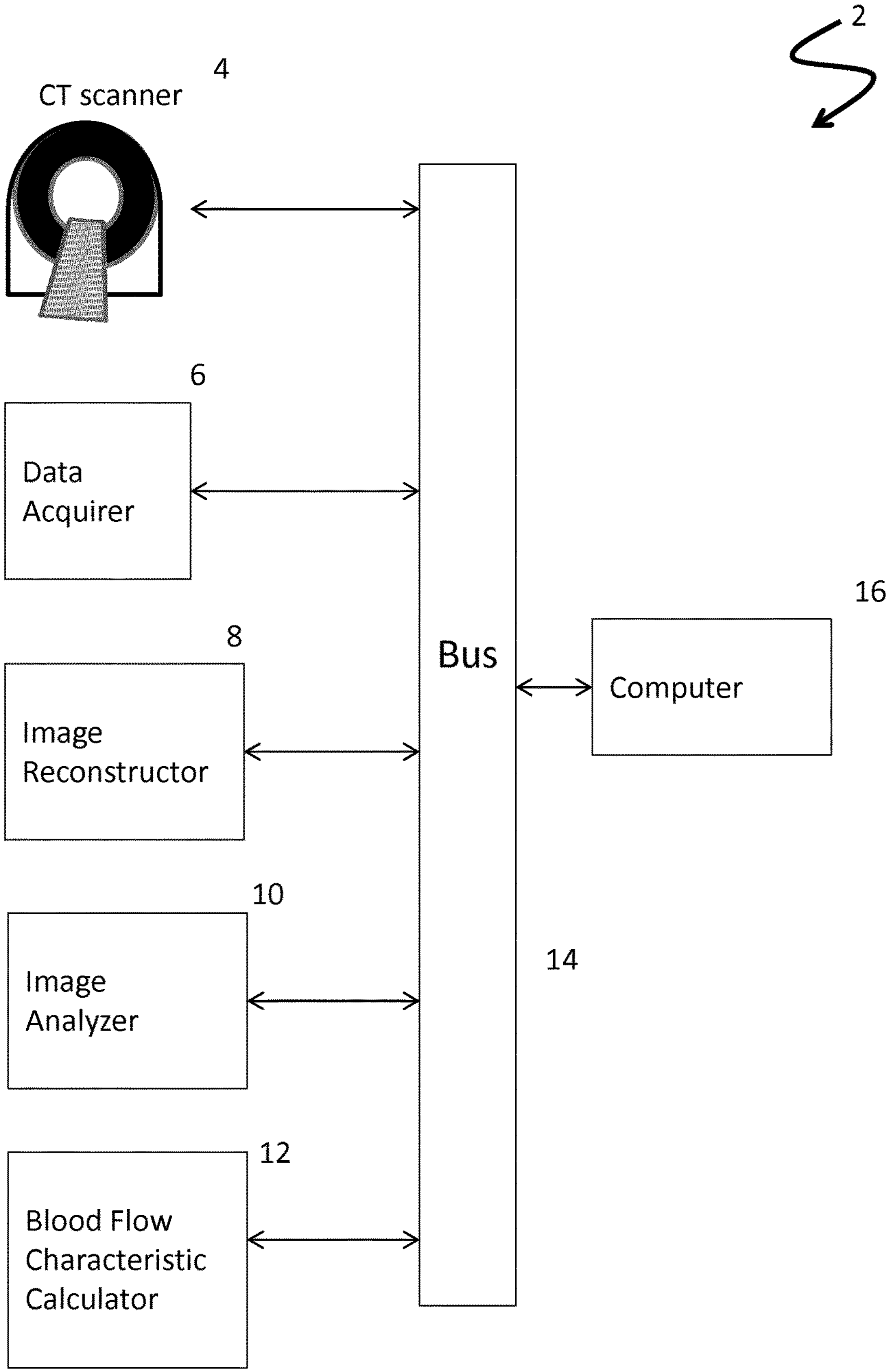
FIG. 1 shows a schematic of a dynamic angiographic imaging (DAI) system.

FIG. 1 shows a computer implemented imaging system, more specifically an example of a DAI system 2, incorporating a computed tomography (CT) scanner 4. The CT scanner 4 may be any multi-row or multi-slice CT scanner typically comprising a radiation source, a radiation detector and an adjustable, often motorized, support or table for maintaining a subject in a desired position (for example, a prone or supine position) during a scan procedure. The radiation source generates radiation that traverses one or more predetermined sampling sites targeting a blood vessel of interest in the subject in synchronization with a contrast agent (also referred to as a tracer) administered to the subject. The radiation detector, often configured as a panel of rotating detectors, receives radiation that traverses the subject at the predetermined sampling site(s) providing projection data (also referred to as scan data) over a time range that encompasses both increase and decrease phases of contrast agent flowing through the blood vessel of interest.

The imaging system 2 includes a data acquisition component 6 incorporating a data acquisition scheme or data acquisition computer code that receives, organizes and stores projection data from the radiation detector of the CT scanner. The projection data is sent to an image reconstruction component 8 incorporating an image reconstruction computer code. The projection data can then be processed using the image reconstruction computer code resulting in image data including multiple images of the predetermined sampling site(s) spanning both increase and decrease phases of contrast agent flowing through the blood vessel of interest. The image reconstruction computer code can easily be varied to accommodate any available CT imaging technique. The image data can then be processed by an image analysis component 10 incorporating image analysis computer code that generates a time-enhancement curve of the contrast signal from the image data. The time-enhancement curve data can then be processed by a blood flow estimation component 12 incorporating a blood flow estimation computer code to determine a blood flow value of the blood vessel of interest from the time-enhancement curve data. The imaging system 2 is controlled by a computer 16 with data and operational commands communicated through bus 14. The imaging system 2 may include any additional component as desired to assess a blood vessel of interest including multiplexers, digital/analog conversion boards, microcontrollers, physical computer interface devices, input/output devices, display devices and the like. The imaging system 2 is shown with a CT scanner as an illustrative example only, and the system may be modified to include other imaging modalities, including for example, X-ray imaging, other than CT, and magnetic resonance imaging (MRI).

Figure 2:
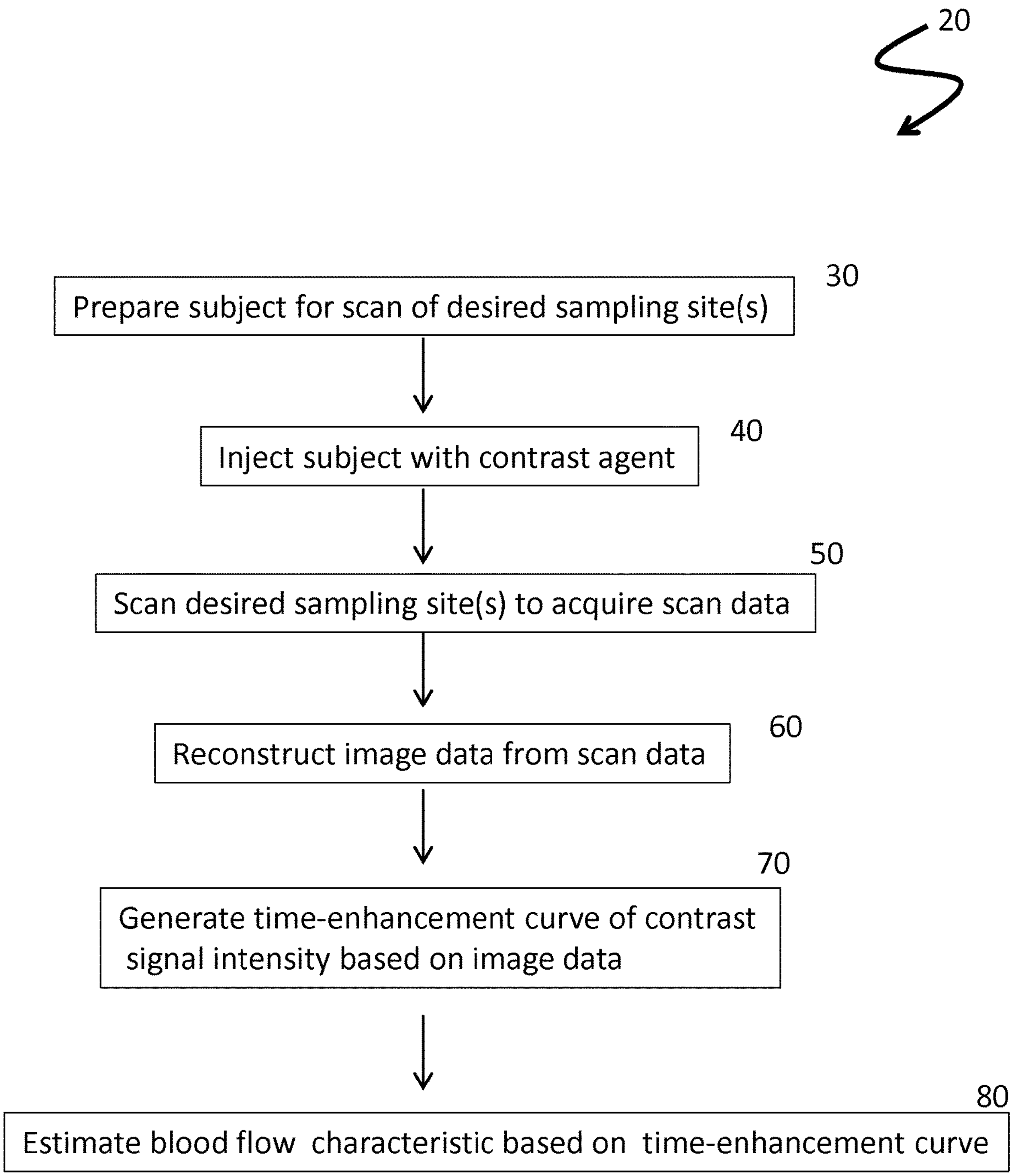
FIG. 2 shows a flow diagram of a DAI method.

FIG. 2 shows a computer implemented method 20 for DAI. The method 20 comprises a pre-scan preparation 30 and positioning of a subject for CT scanning of a desired sampling site. Once the subject is prepared and positioned within a CT scanner, the subject is injected 40 with a contrast agent solution, with CT scanning 50 synchronized with the injection of the contrast agent solution to acquire projection data (also referred to as scan data) over a time range that includes flow of the contrast agent through a blood vessel at the sampling site. The projection data is processed to reconstruct 60 image data from the projection data. The image data is analyzed to generate 70 a time-enhancement curve of a contrast signal parameter, such as contrast signal intensity, extracted from the image data. A blood flow value is calculated 80 based on the time-enhancement curve.

Figure 3:
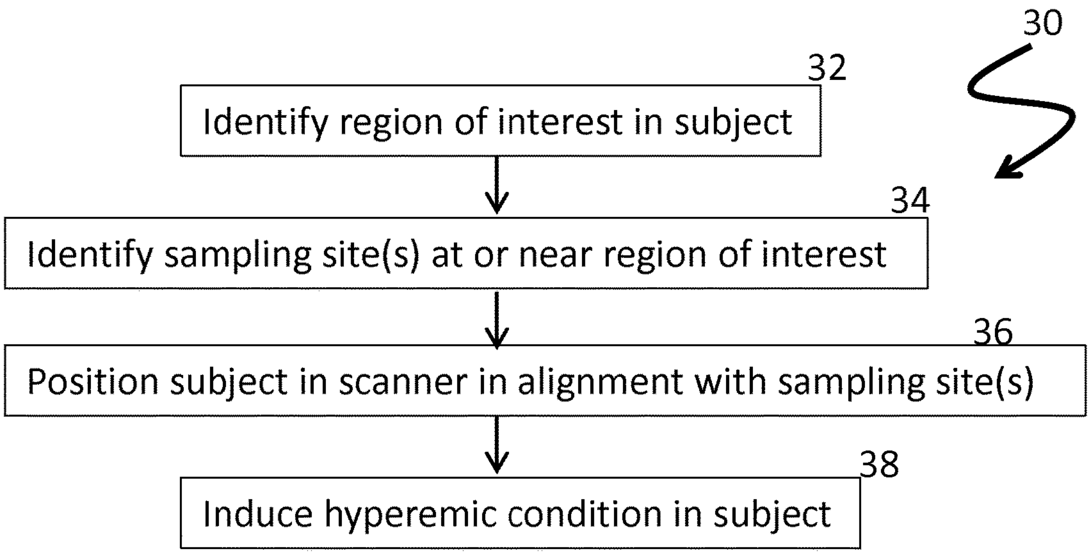
FIG. 3 shows a flow diagram of a pre-scan preparation in the DAI method shown in FIG. 2.

FIG. 3 shows an example of a pre-scan preparation 30 of a subject for CT scanning. The pre-scan preparation 30 includes identifying a region of interest 32 in the subject. For example, the region of interest may be a portion of a blood vessel targeted for assessment of blood flow in the blood vessel. Once a region of interest is established, sampling site(s) for CT scan slices are identified 34 at or near the region of interest. Based on the predetermined sampling site(s), the subject is positioned 36 in the CT scanner in an alignment that allows for a radiation source of the CT scanner to direct radiation at the sampling site(s). Prior to scanning, a hyperemic condition can be induced 38 in the subject, for example by administering a vasodilator to the subject.

Figure 4:
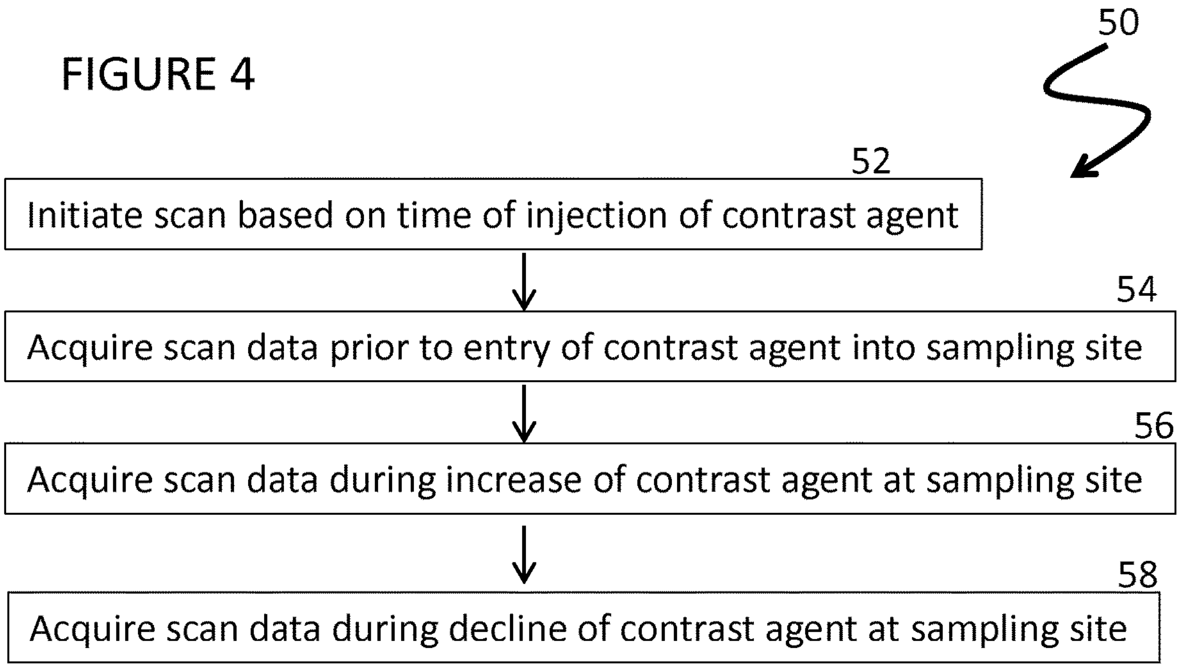
FIG. 4 shows a flow diagram of scan data acquisition in the DAI method shown in FIG. 2.

FIG. 4 shows an example of CT scanning 50 synchronized to injection of the contrast agent. The synchronized CT scanning 50 includes initiating a dynamic CT scan at a desired time based on an injection of the contrast agent. The dynamic CT scan includes acquiring of projection data prior to entry 54 of contrast agent at the sampling site(s), as well as acquiring projection data during an increase phase 56 of the contrast agent at the sampling site(s) and acquiring projection data during a decline phase 58 of the contrast agent at the sampling site. An increase phase refers to an increase of mass of contrast agent at the sampling site as time advances subsequent to initial entry of the contrast agent into the sampling site, while a decline phase or decrease phase refers to a decrease of mass of contrast agent at the sampling site as time advances prior to substantially complete clearance of the contrast agent from the sampling site. Peak (maximum value) mass of contrast agent at the sampling site occurs during progression from the increase phase to the decline phase. Time elapsed from entry to clearance of contrast agent at the sampling site may be referred to as a transit time of the contrast agent. The duration of CT scanning is not limited by a requirement to capture a complete transit time of contrast agent at the sampling site provided that at least a portion of both increase and decrease phases are captured. The projection data acquired prior to entry 54 of the contrast agent can provide a reference value during subsequent image analysis that can be used to normalize contrast agent signal values determined for the increase phase and decline phase.

Figure 5:
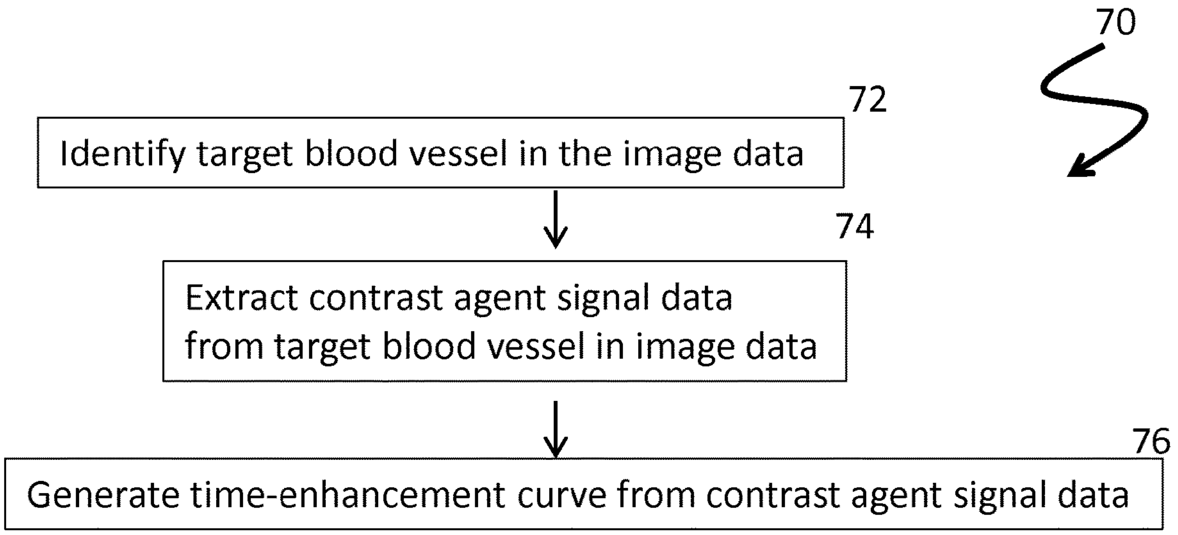
FIG. 5 shows a flow diagram of time-enhancement curve (TEC) generation in the DAI method shown in FIG. 2.

FIG. 5 shows an example of image analysis to generate 70 a time-enhancement curve. Generation of a time-enhancement curve can include identifying 72 a blood vessel of interest within a plurality of corresponding images at a sampling site spanning both the increase and decline phases of contrast agent at the sampling site. Contrast agent signal data is extracted 74, for example contrast agent signal intensity, from an area defined by the blood vessel of interest from each of the plurality of corresponding images. A time-enhancement curve is generated 74 based on the contrast agent signal data during both the increase phase and decline phase at the sampling site. If image data prior to entry of contrast agent at the sampling site is available, then a reference value can be determined to generate a time-enhancement curve based on normalized contrast agent signal values. In alternatives for determining the reference value, scan data prior to entry of contrast agent may be acquired either before or after a contrast agent administration event. As a further alternative, a reference value to normalize a time-enhancement curve can be extracted from image data reconstructed from scan data acquired subsequent to clearance of the contrast agent at the sampling site. Of these alternatives, determining a reference value from scan data acquired after the administration event and prior to entry is typically accomplished with a shorter scan duration. While the time-enhancement curve is generated based on scan data acquired during both the increase phase and decline phase, additionally the time-enhancement curve may optionally be based on scan data acquired during various time points relative to the contrast agent transit time at a sampling site including for example, prior to entry of contrast agent at the sampling site, at peak (maximum value) of contrast agent at the sampling, subsequent to clearance of contrast agent from the sampling site.

Figure 6:
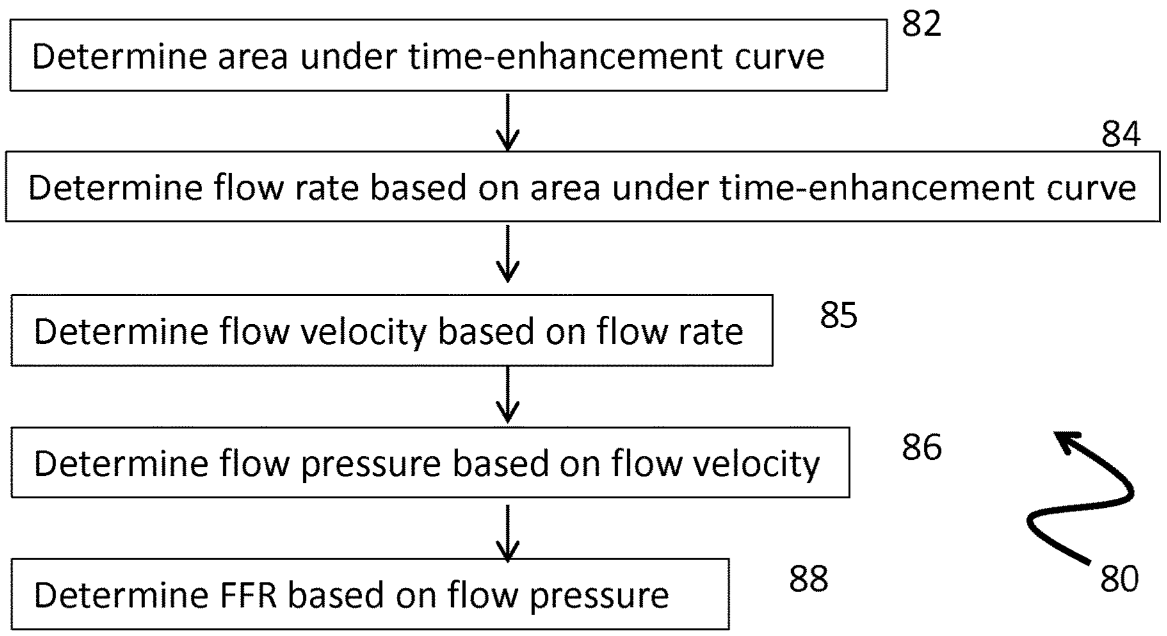
FIG. 6 shows a flow diagram of determining a blood flow characteristic based on the TEC in the DAI method shown in FIG. 2.

FIG. 6 shows an example of estimating blood flow 80 in a blood vessel of interest based on the time-enhancement curve. The estimation of blood flow can be achieved by determining a fractional flow reserve (FFR) value based on the time-enhancement curve. The determination of an FFR value can include calculating an area 82 under the time-enhancement curve. A flow rate 84 can be determined based on the calculated area under the time-enhancement curve, for example using an indicator-dilution principle as expressed in Equation 1 (provided below in an illustrative mathematical basis for the DAI method). A flow velocity can be determined 85 based on the flow rate and a calculated cross-section area of a lumen of the blood vessel at the sampling site, for example using Equation 2 (see below). A flow pressure 86 can be determined from the flow velocity, for example using Bernoulli's equation as expressed in Equations 3A or 3B (see below). Based on flow pressure 86 determined from at least two sampling sites a pressure gradient can be calculated, and an FFR value can be determined based on the calculated pressure gradient and a systolic blood pressure value, for example using Equation 11 (see below). The determined FFR value can be communicated or displayed to a technician/operator or other end-user through any conventional computer or display device.

Figure 8:
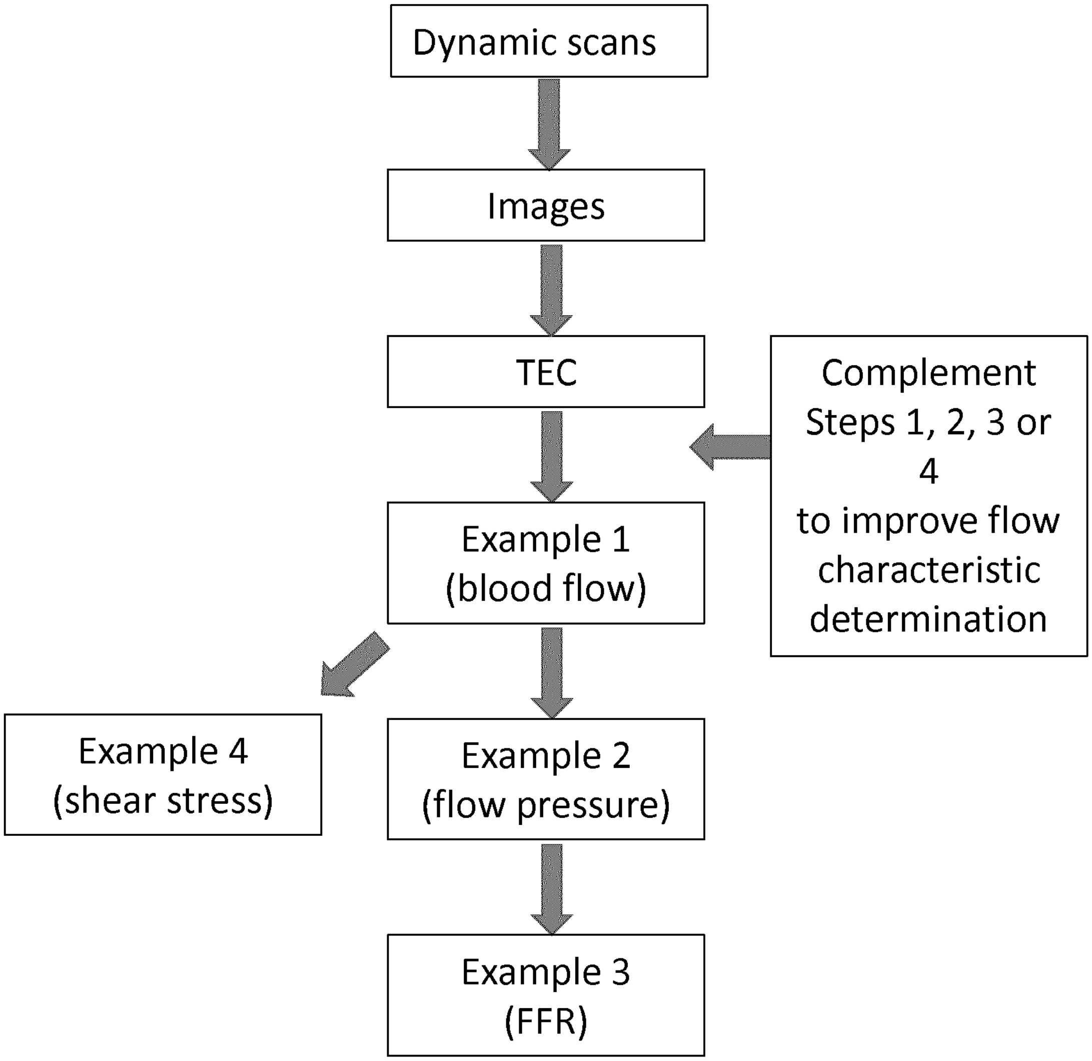
FIG. 8 shows a generalized flow diagram of steps for various examples of determining a blood flow characteristic as well as complement steps for improving determination of a blood flow characteristic.

The DAI system and method have been mathematically validated. Mathematical analysis described in the following paragraphs shows examples of deriving blood flow characteristics in a coronary artery from the contrast-enhanced images of the heart acquired from dynamic imaging. FIG. 8 provides a flow chart showing the relational overview of various examples (Examples 1, 2, 3 or 4) of blood flow characteristic determinations as well as example of additional complement steps (Complement Step 1, 2, 3 or 4) to further improve a blood flow characteristic determination. Detailed description for calculation of each example of a blood flow characteristic and each complement step is provided in the following section. The following mathematical analysis is for illustration purposes only, without wishing to be bound by theory, and is not intended to be a limiting description.

Figure 9:
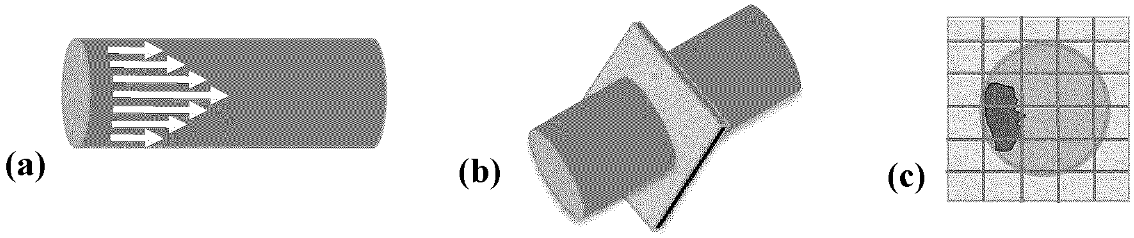
FIG. 9 shows (a) velocity profile of the blood flow in a normal coronary artery; the vector (arrow) representing the magnitude of flow velocity in each layer of flow; (b) a tomographic slice at which a coronary artery is imaged; and (c) the cross-sectional image of a stenosed coronary artery lumen covering a 2×2 pixel region.

Mathematical Analysis: assumptions. Several assumptions may be made about the properties of blood circulating in the coronary system during DAI. First, blood is considered as a Newtonian fluid, which has a linear relationship between shear stress and shear rate; Second, blood flow is laminar under normal condition in which blood moves in parallel layers within the vessel lumen. The layer at the arterial wall surface is stationary (velocity=0), while the layer at the center of the lumen exhibits the highest velocity (FIG. 9*a*). Practically, the blood flow measured at a region of interest within a coronary artery is approximately equal to the average flow rate/velocity around the center; Third, the tracers (also referred to as contrast agent; for example, iodine molecules in CT contrast media) do not leak across the endothelial layer of the coronary artery to the surrounding extravascular spaces during its passage in the artery; Fourth, with the current spatial resolution of CT, the smallest coronary arteries where blood flow can be reliably estimated with the proposed method are those with a diameter greater than 1.5 mm. This is roughly equivalent to a 2×2 pixel region in a CT image (FIGS. 9*b* and 9*c*).

Mathematical Analysis: equation symbols. A summary of the equation symbols used in the mathematical analysis is provided in Table 1. Units listed in Table 1 are not necessarily SI units.

TABLE 1

Summary of equation symbols.

| Symbol | Equation | Description | Unit |
|---|---|---|---|
| F | 1 | volumetric flow rate of blood | mL/s |
| Q | | mass of tracers | mg |
| $C_a$(u) | | arterial concentration of tracers at time u | mg/mL |
| V | 2 | flow velocity of blood | cm/s |
| R | | radius of blood vessel | cm |
| P | 3 | flow pressure | mmHg |
| *P* | | density of blood | g/cm$^3$ |
| G | | Earth's gravity | cm/s$^2$ |
| H | | vertical distance from a reference plane | cm |
| ΔP | | flow pressure difference between slices A and B | Pa |
| $P_L$ | | flow pressure loss | Pa |
| $P_{LF}$ | 4 | flow pressure loss due to friction | Pa |
| $P_{LE}$ | | flow pressure loss due to turbulence | Pa |
| D | 5 | diameter of blood vessel | cm |
| L | | distance between slices A and B | cm |
| F | | Darcy fiction factor | — |
| Re | 6 | Reynolds number | — |
| ε | | surface roughness | cm |
| μ | 7 | blood viscosity | g/cm · s |
| SBP | 11 | systolic blood pressure | mmHg |
| Γ | 12 | stress rate | s$^{-1}$ |
| T | 13 | shear stress | Pa |
| v | 15 | volume of section in a blood vessel | mL |
| l | | length of section in a blood vessel | cm |
| x | 16 | maximum contrast enhancement | HU |

Mathematical Analysis: Method Example 1 in FIG. 8—calculation of coronary blood flow. Coronary blood flow is measured using the indicator-dilution principle, which indicates the degree of which tracer molecules (CT contrast media) mixed with blood after a bolus injection is dependent on the volumetric flow rate of blood. Mathematically, it can be expressed as:

$$F = \frac{Q}{\int_0^t C_a(u)du} \tag{1}$$

where F is the volumetric flow rate of blood (in mL/s), Q is the total mass of tracers (in mg) in a coronary artery, and $C_a$(u) is the tracer concentration in the arterial blood (in mg/mL) at time u. The integral of $C_a$(u) can be determined from the area under the arterial time-enhancement curve (TEC in FIG. 8) acquired from dynamic perfusion imaging, provided proper conversion from contrast enhancement (in Hounsfield unit or HU) to contrast concentration (in mg/mL; 1 mg/mL≈25 HU when the scan setting is 100 kV tube voltage). Q can be derived from a two-step process: first, calculate the total mass of iodine injected into the patient, which equals the product of contrast concentration and injected volume; second, estimate the percentage of iodine entering into the coronary system with either a published value or the information presented in the dynamic perfusion images.

Figure 10:
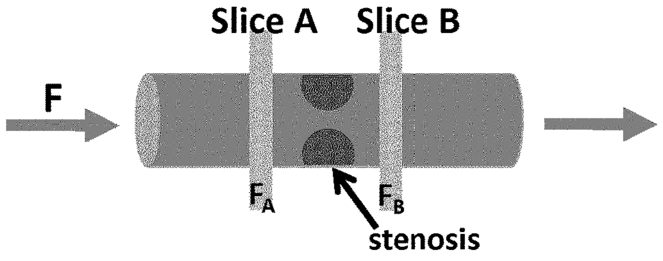
FIG. 10 shows a schematic diagram of two tomographic slices A and B adjacent to a stenosis in a coronary artery; $F_A$ and $F_B$ denote the coronary blood flow in these slices respectively.

Mathematical Analysis: Method Example 2 in FIG. 8—calculation of coronary flow pressure. To estimate the difference in flow pressure across a coronary stenosis, the coronary blood flow is measured before/upstream and after/downstream the stenosis of interest. Consider FIG. 10 which depicts two sampling slice locations A and B adjacent to a stenosis in a coronary artery. At each slice location, coronary blood flow F can be calculated using Eq. 1. Once $F_A$ and $F_B$ are calculated, volumetric flow rate F can be converted to flow velocity V as follows:

$$V = \frac{F}{\pi r^2} \tag{2}$$

where V is the flow velocity (in cm/s) and r is the radius of the blood vessel in cm. The flow pressure difference across the stenosis can be then estimated using the Bernoulli's equation:

$$P_A + \frac{1}{2}\rho V_A^2 + \rho g h_A = P_B + \frac{1}{2}\rho V_B^2 + \rho g h_B + P_L \tag{3a}$$

$$\Delta P = P_B - P_A = \frac{1}{2}\rho\left(V_A^2 - V_B^2\right) + \rho g(h_A - h_B) - P_L \tag{3b}$$

where $P_A$ and $P_B$ are the coronary flow pressure (in Pascal or Pa) in slice A and B respectively, ρ is the density of blood (g/cm$^3$), g is the Earth's gravity (980 cm/s$^2$), $h_A$ and $h_B$ are the relative height (in cm) above or below a reference plane from the center point in slice A and B, and $P_L$ is the pressure (energy) loss due to friction and/or turbulence (see Eq. 4).

Figure 11:
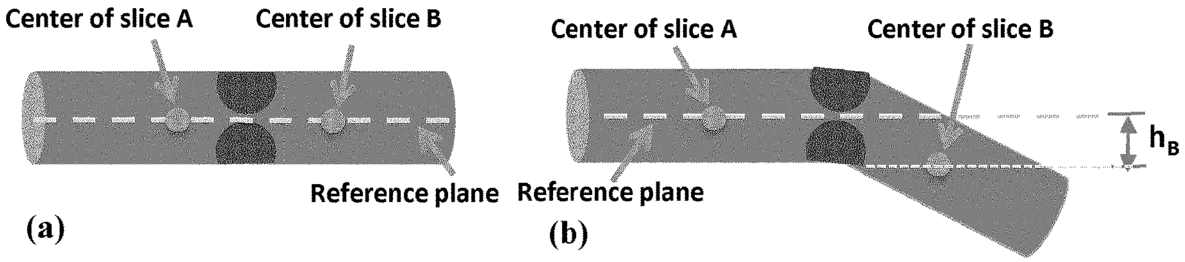
FIG. 11 shows (a) the reference plane (dotted line) and center of lumen in slice A and B in a straight blood vessel; $h_A$ and $h_B$ are zero in this case; and (b) a curved blood vessel, where the reference plane passes through center A and not center B, hence $h_A$ is zero but $h_B$ is not (negative in this case).

The underlying basis of Bernoulli's principle is conservation of energy. The first term in each side of Eq. 3A can be considered as the pressure energy per unit volume, the second term as the kinetic energy per unit volume, and the third term as the potential energy per unit volume. $h_A$ and $h_B$ in the potential energy term can be simplified with proper selection of the reference plane. If the reference plane is chosen to be the plane that passes through the center of lumen in slice A and B, as depicted in FIG. 11*a*, then both potential energy terms in the equation equals zero (i.e. $h_A$ and $h_B$=0). However, if there is a vertical gradient between the two centers, as in the case of coronary anatomy (FIG. 11*b*), then the difference in height between the two centers has to be accounted for. A plane that passes through center A can be chosen as the reference plane so that $h_A$ is always zero and the potential energy term associated with slice A ($\rho g h_A$) can be omitted from Eq. 3 for simplicity. It should be noted that $h_B$ is positive if center B is above center A, and vice versa.

The pressure loss $P_L$ is mainly contributed by friction arising from the movement of viscous blood along the vessel ($P_{LF}$), and to a smaller extent by the eddies (swirling flow) generated from the sudden expansion in lumen when flow moves from a stenosed coronary segment to a normal segment ($P_{LE}$):

$$P_L \approx P_{LF} + P_{LE} \tag{4}$$

The magnitude of $P_{LF}$ can be estimated using the Darcy-Weishbach equation:

$$P_{LF} = f\left(\frac{L}{D}\right)\left(\frac{\rho V^2}{2}\right) \tag{5}$$

where L is the distance between slice A and B (in cm), D is the diameter of the artery (in cm) and V as given by Eq. (2) is the average flow velocity between slice A and B. The Darcy friction factor f is a dimensionless quantity and is given by the Churchill equation:

$$f = 8\left[\left(\frac{8}{\mathrm{Re}}\right)^{12} + \frac{1}{(c+D)^{1.5}}\right]^{\frac{1}{12}} \tag{6}$$

$$\text{where } C = \left[2.457 \ln\left(\frac{1}{\left(\frac{7}{\mathrm{Re}}\right)^{0.9} + 0.27\frac{\varepsilon}{D}}\right)\right]^{16} \text{ and } D = \left(\frac{37530}{\mathrm{Re}}\right)^{16}$$

where Re is the Reynolds number that predicts the flow behavior (laminar versus turbulent flow), $\varepsilon$ is the roughness metric which describes the surface texture of the pipe where the fluid flows. Blood vessels are assumed to be smooth pipes and hence $\varepsilon$ is zero. The Reynolds number is given by:

$$\mathrm{Re} = \frac{\rho D V}{\mu} \tag{7}$$

where $\mu$ is the blood viscosity in Pa·s or kg/m·s or g/cm·s. Alternatively, the Darcy friction factor can also be estimated using the following equations:

For laminar flow:

$$f = \frac{64}{\mathrm{Re}} \tag{8}$$

For turbulent flow:

$$\frac{1}{\sqrt{f}} = 1.74 - 2.0\ \log_{10}\left[\frac{\varepsilon}{r} + \frac{18.7}{\mathrm{Re}\sqrt{f}}\right] \tag{9}$$

$$= 1/74 - 20\ \log_{10}\left[\frac{18.7}{\mathrm{Re}\sqrt{f}}\right] \text{ when } \varepsilon = 0$$

Eq. (9) is also known as the Colebrook equation. The choice of Eq. (8) or (9) depends on the flow behavior (laminar versus turbulent), which can be estimated using the Reynolds number obtained from Eq. (7). In general, blood flow is fully laminar when Re<2000 and fully turbulent when Re>4000. The magnitude of $P_{LE}$ in Eq. (4) can be estimated as:

$$P_{LE} = \frac{(V_1 - V_2)^2}{2\text{ g}} \tag{10}$$

where $V_1$ and $V_2$ are the flow velocities in the narrowed segment and adjacent normal segment (exit) respectively. The other factor that could contribute to the minor pressure loss is the flow entrance from a larger vessel to a smaller vessel. As the loss coefficient associated with well-rounded (non-sharp) pipe entrance is very small (0.04), the minor pressure loss due to flow entrance may be assumed to be negligible compared to the minor pressure loss due to sudden lumen expansion as depicted in Eq. (10).

For proper application of the Bernoulli's equation the unit in each term should be consistent to the others. All the energy terms (pressure, kinetic and potential) in the equation should have a unit of $(g \cdot cm^2 \cdot s^{-2})/cm^3$. The pressure unit is Pascal, which can be first converted to the following unit: 1 Pa=1 kg/m·$s^2$=1000 g/100 cm·$s^2$=10 g/cm·$s^2$. After estimating the pressure gradient $\Delta P$ in g/cm·$s^2$, we can then convert it to the conventional mmHg unit with a multiplication factor of 0.0075 (1 Pa=0.0075 mmHg).

Mathematical Analysis: Method Example 3 in FIG. 8—calculation of fractional flow reserve. Fractional flow reserve (FFR) can be derived from $\Delta P$ in Eq. (3b). In routine clinical practice, $P_A$ is assumed to be identical to the systolic blood pressure (SBP) which can be obtained from the mean arterial pressure measurement. Thus, FFR can be estimated by the following equation:

$$FFR = \frac{P_B}{P_A} = \frac{\Delta P + SBP}{SBP} \tag{11}$$

Mathematical Analysis: Method Example 4 in FIG. 8—calculation of shear stress. From the blood flow measurement in Example 1 in FIG. 8, the wall shear stress can also be estimated. The wall shear stress is the shearing force exerted to the arterial wall surface by blood flow. This parameter may be useful for predicting the vulnerability of a plaque developed on the wall surface of an artery. Blood moves in parallel layers in a blood vessel due to its laminar behavior, with the flow velocity equaling zero at the surface of the vessel wall. Shear rate describes the rate at which different blood layers move past each other, and the wall shear rate specifically refers to the rate at which a blood layer of interest moves relative to the blood layer at the wall surface that has a zero velocity. If the blood layer of interest passes through the center of the vessel lumen, then the wall shear rate $\gamma$ (in $s^{-1}$) can be approximately given by:

$$\gamma = \frac{V}{r} = \left(\frac{F}{\pi r^2}\right) \cdot \frac{1}{r} = \frac{F}{\pi r^3} \tag{12}$$

where r is the radius of the blood vessel (the distance between the center layer and wall surface), V is the flow velocity of the center blood layer relative to the wall surface, and F is the volumetric flow rate of blood at the center of the vessel. Practically, blood flow is measured in a region that covers more than just the center of the vessel and the measurement can be approximated as the average flow rate or velocity at the center for simplicity. Since blood is a Newtonian fluid, its shear rate is linearly related to the shear stress:

$$\tau = \mu \cdot \gamma \tag{13}$$

where τ is the shear stress in Pascal (Pa), and μ is the blood viscosity (in g/cm·s). Both viscosity and density may be measured from a blood test instead of using the published values for average adults to improve the accuracy of the calculation for individual patients.

Mathematical Analysis: Method Complement Step 1 in FIG. 8—estimation of the mass of tracers entering the coronary circulation from the aorta. Coronary blood flow (F) is estimated from Eq. (1), which requires prior knowledge of the mass of tracers (Q). After a bolus injection into a peripheral vein (e.g. antecubital vein), all the tracers are delivered to the heart chambers where they are uniformly mixed and ejected into the ascending aorta. Hence, the amount of tracers delivered to each organ via the arterial blood can be estimated from the ratio of the organ blood flow to the total cardiac output. For instance, blood flow in the heart is about 5% of the cardiac output, hence we can assume that 5% of the injected tracers are delivered to the coronary arteries.

This section presents a Complement step where information present in the dynamic perfusion images can be used to estimate the mass of tracers in the coronary system. Using patient-specific information may allow a more accurate measurement of coronary flow and pressure for individual patients.

Unlike most vascular beds in the body, blood flow in the coronary arteries is at maximum during diastole rather than systole. During diastole, the left ventricle continues to relax, leading to a substantial decrease in the aortic pressure and backflow in the aorta. At the same time, there is a relief of compression of the coronary microcirculation in the myocardium. Consequently, a backflow (e.g., backward-propagating suction) is generated which facilitates the filling of coronary arteries. Hence, the backflow in the aorta together with the decrease in coronary resistance leads to the maximal coronary blood flow at diastole. In dynamic myocardial perfusion imaging, contrast-enhanced heart images are acquired at consecutive diastoles to minimize cardiac motion, hence the aortic flow observed in these dynamic images are retrograde (backward) flow instead of antegrade (forward) flow. The direction of flow is illustrated in FIG. 12.

Figure 12:
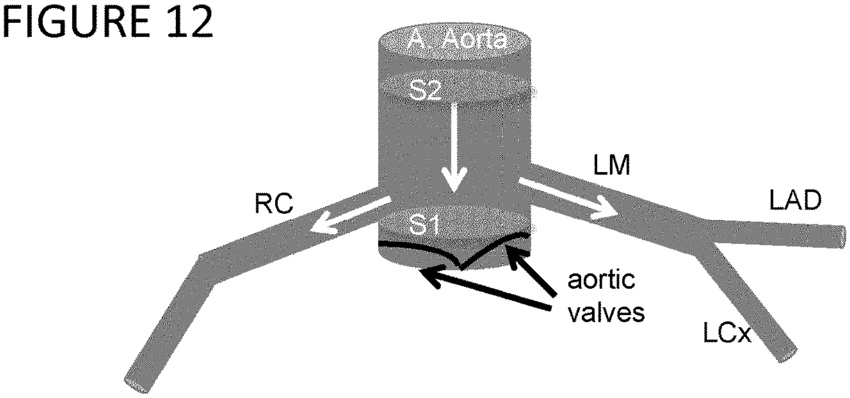
FIG. 12 shows a schematic of the ascending aorta and coronary arteries.

Consider two tomographic slices in the ascending aorta shown in FIG. 12. Slice 1 (S1) locates just above the orifice and aortic valves, and slice 2 (S2) is several centimeters above S1 but below the aortic arch (not shown in FIG. 12). The blood flow in each slice can be estimated using the indicator-dilution principle as shown in Eq. (1):

$$F_1 = \frac{Q_1}{\int_0^t C_{a1}(u)du} \tag{1a}$$

$$F_2 = \frac{Q_2}{\int_0^t C_{a2}(u)du} \tag{1b}$$

where $F_1$ and $F_2$ are the volumetric flow rate (in mL/s) in slice 1 and 2 respectively, $Q_1$ and $Q_2$ are the mass of tracers (in mg) in slice 1 and 2 respectively, and the integral of $C_{a1}(u)$ and $C_{a2}(u)$ are the area under the time-enhancement curves measured in slice 1 and 2, respectively, from time 0 to t. Given the fact that the aortic blood flow is very fast and the two slices are relatively close to each other, it can be assumed that the blood flow is identical in both slices, i.e. $F_1=F_2$. Combining Eq. (1a) and Eq. (1b) yields:

$$\frac{Q_1}{\int_0^t C_{a1}(u)du} = \frac{Q_2}{\int_0^t C_{a2}(u)du} \quad \text{or} \quad \frac{Q_1}{Q_2} = \frac{\int_0^t C_{a1}(u)du}{\int_0^t C_{a2}(u)du} \tag{14}$$

Eq. (14) describes the fraction of tracers in slice 1 with respect to that in slice 2. Since some tracers passing through slice 2 enter the coronary arteries before reaching slice 1, $Q_1$ should be smaller than $Q_2$. As blood flow in the heart is about 5% of the cardiac output, roughly 5% of the tracers leaving the heart should end up in the coronary circulation. If the tracers ejected from the heart are uniformly distributed along the aorta, $Q_1/Q_2$ should be approximately equal to 0.95 ($Q_1$ is about 95% of $Q_2$. See experimental testing examples).

Figure 13:
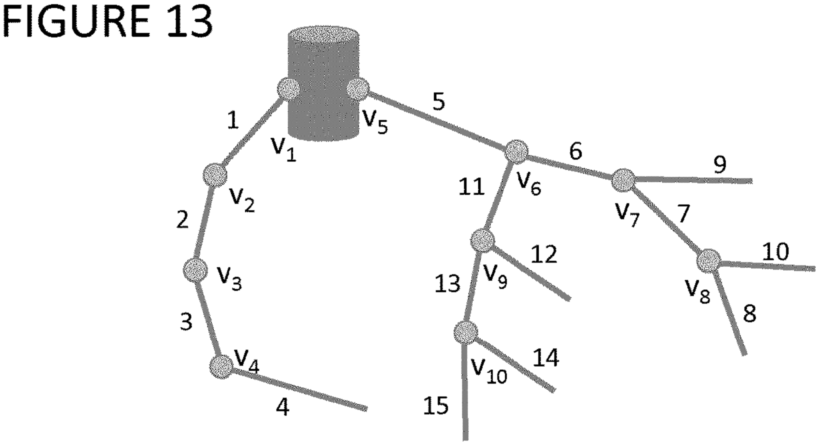
FIG. 13 shows a graphical representation of the coronary artery system.

Mathematical Analysis: Method Complement Step 2 in FIG. 8—estimation of the mass of tracers in individual coronary arteries. Similar to mathematical treatment of Complement Step 1 in FIG. 8, this section describes a method for the estimation of the mass of tracers in each epicardial coronary artery based on the information present in the dynamic perfusion images. A graphical representation of the coronary artery system can facilitate a description of Complement Step 2. The vasculature in any organ, such as the coronary artery system in the heart, can be represented by a graph with multiple edges and vertices such as shown in FIG. 13.

A vertex (v) can be viewed as the intersection connecting two (or more) blood vessels together, whereas an edge (E) can be viewed as the blood vessel that connects two vertices together. Mathematically, the graph shown in FIG. 12 can be expressed as:

$$v=\{v_1, \ldots, v_n\} \text{ where } n=10;$$

$$E=\{\{v_1,v_2\},\{v_2,v_3\},\{v_3,v_4\},\{v_5,v_6\},\{v_6,v_7\},\{v_7,v_8\},\{v_6,v_9\},\{v_9,v_{10}\}\}.$$

This graph is a directed graph in which the net flow in each edge is one direction only (not bi-directional). The flow usually moves in the direction away from the source (the aorta as represented by the dark grey cylinder in the graph). Each edge is assigned a number (as specified in Table 2) according to the American Heart Association model for the coronary arteries:

TABLE 2

| Numbering model for coronary arteries. |
|---|
| 1—proximal right coronary (RC) |
| 2—mid RC |
| 3—distal RC |
| 4—posterior descending |
| 5—left main (LM) |
| 6—proximal left anterior descending artery (LAD) |
| 7—mid LAD |
| 8—distal LAD |
| 9—1st diagonal |
| 10—2nd diagonal |
| 11—proximal left circumflex (LCx) |
| 12—obtuse marginal |
| 13—distal LCx |
| 14—posterolateral |
| 15—posterior descending |

Figure 14:
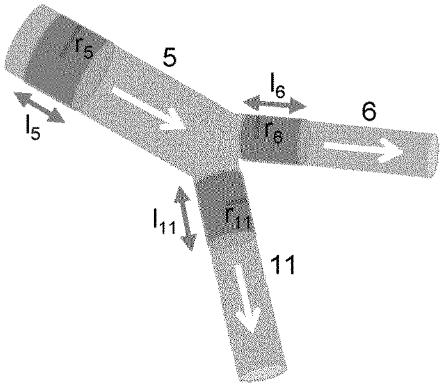
FIG. 14 shows a schematic of three edges and their intersection from the representation of the coronary artery system shown in FIG. 13.

To illustrate how the distribution of tracers in each coronary artery is estimated, consider three edges: 5, 6 and 11, which represent the LM and proximal LAD and LCx, respectively. Edge 5 is the "parent" vessel of edges 6 and 11, and edges 6 and 11 are the "daughter" vessels of edge 5. These vessels are connected at vertex 6 ($v_6$). FIG. 14 shows a schematic representation of the three edges and their intersection.

The direction of flow in each blood vessel is illustrated by a white arrow in FIG. 14. In each blood vessel, a section close to the entrance is highlighted in dark grey colour. The radius (r) and length (l) of each section are labeled with the subscript (n) equals the edge number of the vessel. The volume of each section ( ($\mathcal{V}_n$)) is given by:

$$\mathcal{V}_n = \pi r_n^2 l_n \tag{15}$$

To avoid confusion, "V" represents the flow velocity (cm/s); "v" represents the vertex (intersection); "$\mathcal{V}$" represents the volume of vessel section. The volume of each section has a unit of $cm^3$ and can be converted to mL.

Figure 15:
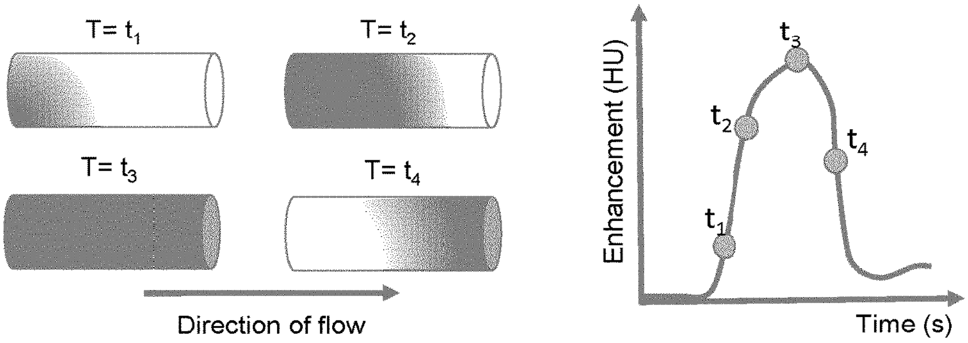
FIG. 15 shows a schematic correlating mass of contrast agent in a vessel section to different time points of a corresponding measured time-enhancement curve.

Consider the two highlighted sections in edges 5 and 6. As depicted in FIG. 15, all tracers (represented by the grey colour in the vessel) remain in the section at the time corresponding to the peak of the time-enhancement curve measured in that section ($T=t_3$, FIG. 15). The maximum value (peak value) of the time-enhancement curve has a unit of HU (Hounsfield Unit) and can be converted to (mg/mL).

As such, the total mass of tracers in a given section of the vessel (Q, in mg) can be estimated by multiplying the maximum value (peak value) of the time-enhancement curve measured in the section (x, in mg/mL) by the volume of the section:

$$Q_n = \mathcal{V}_n \cdot x_n \tag{16}$$

where n is the edge number. The fraction of tracers going from edge 5 (LM) to edge 6 (LAD) can be calculated by taking the ratio of $Q_6$ and $Q_5$:

$$\frac{Q_6}{Q_5} = \frac{\mathcal{V}_6 \cdot x_6}{\mathcal{V}_5 \cdot x_5} = \frac{(\pi r_6^2 l_6) \cdot x_6}{(\pi r_5^2 l_5) \cdot x_5} = \frac{r_6^2 l_6 x_6}{r_5^2 l_5 x_5} \tag{17}$$

If the length of each section is identical, i.e. $l_5=l_6$, then Eq. (17) can be further simplified to:

$$\frac{Q_6}{Q_5} = \left(\frac{r_6}{r_5}\right)^2 \cdot \left(\frac{x_6}{x_5}\right) \tag{18}$$

Eq. (18) equals the fraction of tracer distribution in the LAD with respect to the LM. Similarly, the fraction of tracer distribution in the LCx with respect to the LM is given by:

$$\frac{Q_{11}}{Q_5} = \left(\frac{r_{11}}{r_5}\right)^2 \cdot \left(\frac{x_{11}}{x_5}\right) \tag{19}$$

All tracers leaving the LM must be delivered to either the LAD or LCx (in the case of no intermediate branch). Hence, the following equation holds as a consequence of the conservation of mass of tracers in the vasculature:

$$\frac{Q_6}{Q_5} + \frac{Q_{11}}{Q_5} = 1 \tag{20}$$

substituting Eq. (18) and (19) into (20) yields:

$$r_6^2 x_6 + r_{11}^2 x_{11} = r_5^2 x_5 \tag{21}$$

Mathematical Analysis: Method Complement Step 3 in FIG. 8—motion correction for time-enhancement curve. Measurement of time-enhancement curves (TECs) may be affected by residual motion of the coronary arteries. This section describes a set of criteria that may be used to minimize motion-induced fluctuation of the TEC to improve accuracy of the TEC and to facilitate accurate coronary flow and pressure assessment:

1. TEC in a proximal coronary segment can be measured with a larger pixel region to maximize the signal-to-noise ratio of the curve. This high quality TEC can be used as the reference curve to constrain the shape of the TEC measured in a distal segment of the same artery (see criteria #2 and #3 below).
2. As each epicardial coronary artery has only one inlet, the contrast arrival time of a distal (downstream) TEC cannot be shorter than the contrast arrival time of a proximal (upstream) TEC measured in the same coronary artery. Contrast arrival time refers to the time interval between t=0 (first dynamic image coordinated at or near a time of bolus injection) to the moment when the tracers (contrast media) arrive in the artery (contrast enhancement begins).
3. For the reason that each epicardial coronary artery has a single inlet, the area under a distal (downstream) TEC cannot be greater than the area under a proximal (upstream) TEC, as the area under curve (AUC) in a coronary segment is related to the total mass of tracers passing through that segment.
4. The time point that corresponds to the maximum contrast enhancement in a coronary artery is first identified. It is used as the reference time point to track the position of the same artery at all the other time points.
5. In each slice, a small pixel region (e.g. 2×2 pixels) is used to cover the artery of interest at the reference time point (criteria #4). This pixel region is then used to search the same section of the artery at other time points within a larger search area (e.g. 20×20 pixels) in the same slice.
6. For a time point when the artery of interest is not apparent in a slice due to motion, the search area in criteria #5 extends to one adjacent slice above (upstream) and an adjacent slice below (downstream) at the corresponding time point (a scan can capture 3D image data of all or part of a blood vessel, and the 3D image data can be divided into multiple slices so that an adjacent slice above (upstream) and an adjacent slice below (downstream) is readily available to compensate for an artery of interest missing at the time point). If the artery remains missing or is substantially blurred as a result of severe motion, linear interpolation is applied to estimate the missing contrast enhancement value in that section of the artery for that time point of the time-enhancement curve. The reference curve from criteria #1 can be used to make sure the interpolated pixel values do not lead to violation of criteria #2 and 3.

Mathematical Analysis: Method Complement Step 4 in FIG. 8—assessment of the effectiveness of bolus injection of tracers. While all the tracers injected into a peripheral vein should be delivered to the heart, it is possible that the intravenous bolus injection is suboptimal due to technical issues (e.g. malfunction of injection pump, poor positioning of injection needle, or vasoconstriction) and consequently leads to the overestimation of the mass of tracers in the coronary system. This section describes a method that can be used to evaluate the effectiveness of tracer injection from the information present in the dynamic contrast-enhanced images.

The time-enhancement curve (TEC) in the superior vena cava (SVC) is first measured from the dynamic images. SVC is the first pathway where the tracers enter the heart and is closed to the venous injection site. Hence, the tracers appear in the SVC should be minimally diluted or dispersed. Once the TEC is measured from the SVC, the area under curve is calculated before the indictor-dilution principle (Eq. (1)) is applied to estimate the blood flow in the SVC. The average blood flow in SVC for adults is around 1800 to 2000 mL/min. If calculation of SVC blood flow is comparable to the published values, then a determination may be made that all the tracers are properly injected into the peripheral vein. By contrast, if a substantial portion of tracers is not properly injected into the vein, then the TEC measured in the SVC should have a much smaller area under curve and consequently lead to a significant overestimation of the SVC blood flow.

The DAI system and method have been validated by experimental testing. Experimental testing results demonstrate the ability of the DAI system and method to determine one or more of several blood flow characteristics. The following experimental examples are for illustration purposes only and are not intended to be a limiting description.

Experimental Exemplification: Experimental Example 1. The results of Experimental Example 1 are related to the use of mathematical methods described in Example 1 from FIG. 8.

(a) Patient and scan information. Patient #1 was a 62 year old female who weighed 51 kg. She had both rest and stress CT myocardial perfusion imaging. The hyperemic condition was induced with intravenous infusion of dipyridamole. For each imaging study, 36 mL of iodinated contrast (dosage: 0.7 mL of kg body weight) was injected with a contrast concentration of 350 mgI/mL. Dynamic imaging of 120 mm of the heart was performed over 30 mid-diastoles with breath-hold using a 256-row/160-mm clinical CT scanner at 100 kV tube voltage, 100 mA tube current and 280 ms gantry rotation speed.

Figure 16:
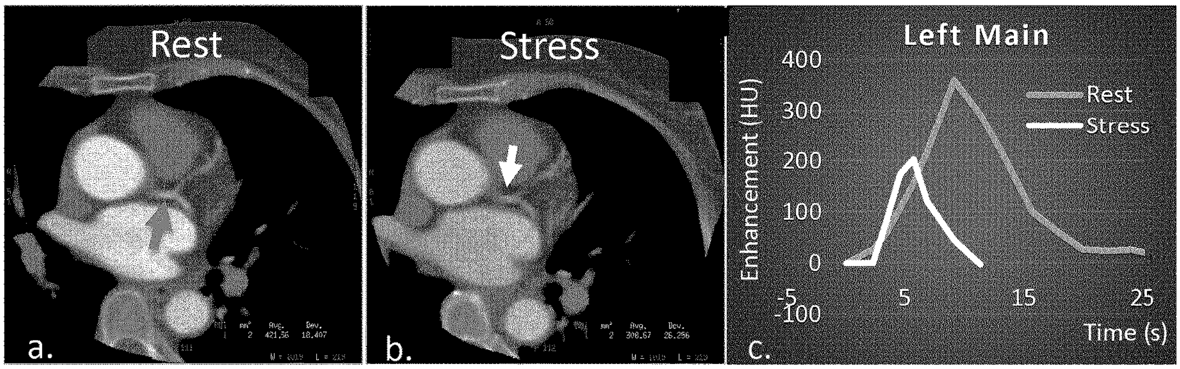
FIG. 16 shows ((a) and (b)) contrast-enhanced CT heart images at rest and during vasodilatory (dipyridamole) stress; (c) comparison of the time-enhancement curves (TECs) measured in the left main artery at rest (grey curve) and during maximal vasodilatory stress (white curve); the two TECs are aligned to the same start time to facilitate shape comparison.

(b) Figures. FIGS. 16*a* and 16*b* show the contrast-enhanced image of the heart acquired at rest and during maximal vasodilatory stress, respectively, at the slice location where the left main artery was seen. The time-enhancement curves measured from the left main artery before the bifurcation (arrows in FIG. 16*a/b*) are shown in FIG. 16*c*.

(c) Results. CT coronary angiography (CCTA) revealed no stenosis in all the coronary arteries including the left main artery. The corresponding myocardial perfusion measurement with SPECT (single photon emission computed tomography) and CT showed no ischemia in the myocardium. The AUC of the left main TEC (area under curve) at rest and stress was 3104.87 and 1350.35 HU·s respectively. The corresponding coronary blood flow at rest and stress were 100.61 and 231.33 mL/min respectively. The ratio of stress to rest coronary blood flow (i.e. coronary flow reserve) was 2.31.

(d) Interpretation. It is well documented that coronary blood flow can increase by 2 to 4 times from baseline during maximal coronary vasodilation in non-ischemic myocardium. Our data showed that the increase in coronary blood flow from baseline as measured by our method agreed with the expected range for normal coronary territory. Hence, the findings from this study suggested that our method was able to reliably measure resting and hyperemic coronary blood flow.

Experimental Exemplification: Experimental Example 2. The results of Experimental Example 2 are related to the use of mathematical methods described in Examples 1-3 from FIG. 8.

(a) Patient and scan information. Patient #2 was a 62 year old female who weighed 60 kg. She underwent a stress CT myocardial perfusion imaging at 3 minutes into an intravenous infusion of adenosine (vasodilator) at a rate of 140 $\mu g \cdot kg^{-1} \cdot min^{-1}$. During the imaging study, 43 mL of iodinated contrast (dosage: 0.7 mL of kg body weight) was injected with a contrast concentration of 320 mgI/mL. Dynamic imaging of 120 mm of the heart was performed with a 256-row/160-mm clinical CT scanner over 22 mid-diastoles at 100 kV tube voltage, 100 mA tube current and 280 ms gantry rotation speed. The patient was holding her breath throughout the imaging study. The recorded mean arterial pressure at 3 min into adenosine infusion was 132/78 mmHg.

Figure 17:
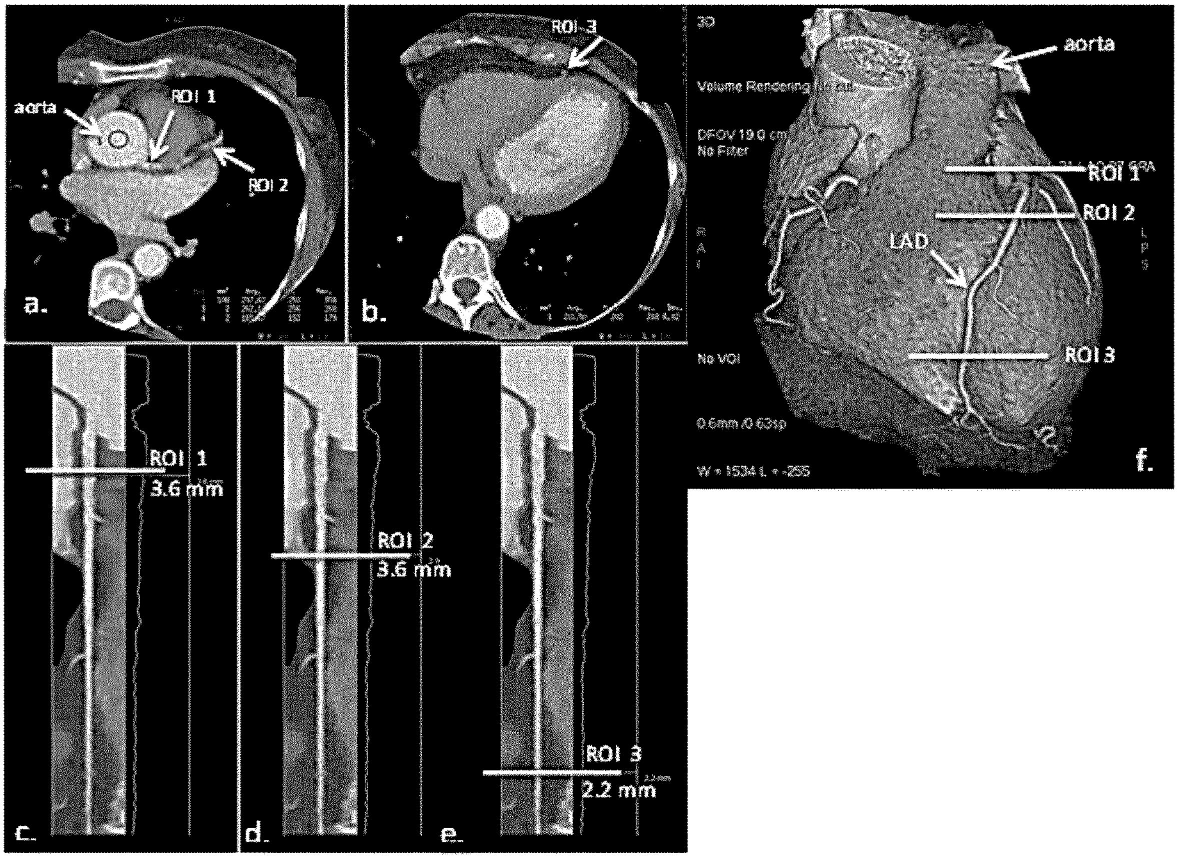
FIG. 17 shows ((a) and (b)) contrast-enhanced heart images at the two slices where time-enhancement curves in the left main (LM) artery and left anterior descending (LAD) artery were measured; ((c) to (c)) reformatted lumen view of the LM and LAD with the location of each ROI and the corresponding lumen diameter labelled; (f) three-dimensional rendered image of the heart with the approximate location of each ROI labelled.
Figure 18:
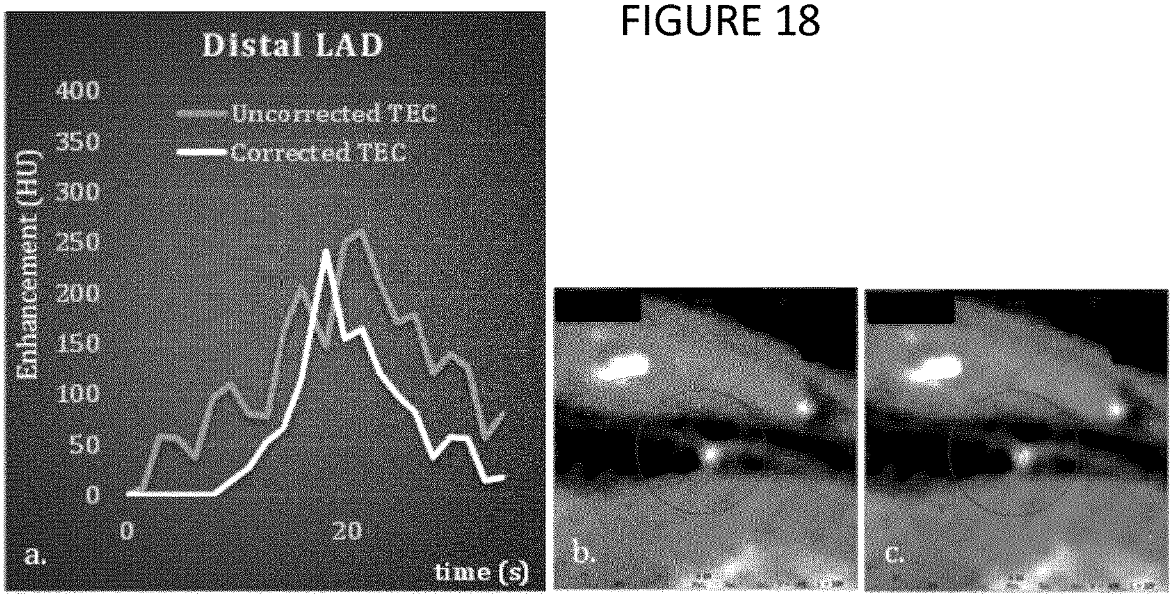
FIG. 18 shows (a) a comparison of TEC measured in the distal LAD shown in FIG. 17*b* without and with motion correction; ((b) and (c)) cross-sectional view of the distal LAD to illustrate the alignment of vessel lumen before (b) and after (c) motion correction was applied; TEC was measured in a 2×2 square pixel region, and a larger pixel region (20×20 pixels) was used to monitor the movement of LAD at different time points for motion correction.

(b) Figures. FIGS. 17*a* and 17*b* show the contrast-enhanced heart images at two axial slices to illustrate where the TEC was measured in the left main (LM, ROI 1) and proximal (ROI 2) and distal (ROI 3) LAD. The slice locations were 60 mm apart. FIGS. 17*c*, 17*d* and 17*e* show the reformatted lumen view of the LAD to illustrate the location of each ROI shown in FIGS. 17*a* and 17*b*. The lumen diameter at each location was also labelled. FIG. 17*f* shows the three-dimensional rendered image of the heart with the approximate location of each ROI. FIG. 18 show the TEC measured in the distal segment of the LAD without and with motion correction (Complement Step 3 in FIG. 8).

(c) Results. CCTA showed no stenosis in the LM and LAD arteries. FFR in the proximal and distal segments of the LAD were 0.99 and 0.92 respectively. The findings are summarized in Table 3.

TABLE 3

| Summary of physiological measurements in the LAD artery of patient#2. | | | | | | | |
|---|---|---|---|---|---|---|---|
| | Lumen diameter (cm) | Coronary blood flow (mL/min) | Degree of stenosis (% lumen narrowing) | Reynolds number | Turbulent flow | Pressure drop from ROI 1 (ΔP, mmHg) | Fractional flow reserve (FFR) |
| LM (ROI 1) | 0.36 | 333.21 | — | 512.5 | N | — | — |
| Prox LAD (ROI 2) | 0.29 | 337.92 | — | 649.1 | N | −1.12 | 0.99 |
| Distal LAD (ROI 3) | 0.22 | 366.78 | — | 928.7 | N | −11.21 | 0.92 |

(d) Interpretation. Given the high sensitivity and negative predictive value of CCTA, we can be sure that the LM and LAD arteries were normal (without stenosis). The FFR measurement with our method suggested that there was no significant decrease in the flow pressure along the LAD artery, which agreed with the anatomic assessment of CCTA. Furthermore, the coronary blood flow during maximal vasodilation (>330 mL/min) was much higher than the reported resting coronary blood flow in normal subjects (~200 mL/min), and was relatively consistent between the proximal and distal segments of the LAD. This study demonstrated that the FFR assessment with our method agreed well with the anatomical assessment with CCTA. Additionally, the study also suggested that FFR measurement in a distal coronary artery with a diameter of merely 2 mm is feasible provided proper motion correction to the TEC is applied. Before motion correction, the AUC in the distal LAD was 4302.5 HU·s and was much higher than that in the proximal LAD (2512.9 HU·s). The AUC is closely related to the amount of tracers and it does not make sense if the distal segment has more tracers than in the proximal segment of the same artery. After proper motion correction, the AUC in the distal LAD became slightly lower compared to the proximal LAD, which seems more reasonable. The slightly lower AUC in the distal LAD was due to the loss of some tracers through small arterial branches between the proximal and distal LAD.

Experimental Exemplification: Experimental Example 3. The results of Experimental Example 3 are related to the use of mathematical methods described in Examples 1~4 from FIG. 8.

(a) Patient and scanning information. Patient #3 was a 59 year old male who weighed 102 kg. He underwent a stress CT myocardial perfusion imaging at 3 min into an intravenous infusion of adenosine (vasodilator) at a rate of 140 $\mu g \cdot kg^{-1} \cdot min^{-1}$. During the imaging study, 70 mL of iodinated contrast (dosage: 0.7 mL of kg body weight) was injected with a contrast concentration of 320 mgI/mL. Dynamic imaging of 120 mm of the heart was performed with a 256-row/160-mm clinical CT scanner over 25 mid-diastoles at 100 kV tube voltage, 100 mA tube current and 280 ms gantry rotation speed. The patient was holding his breath throughout the imaging study. The recorded mean arterial pressure at 3 min in adenosine infusion was 124/60 mmHg.

Figure 19:
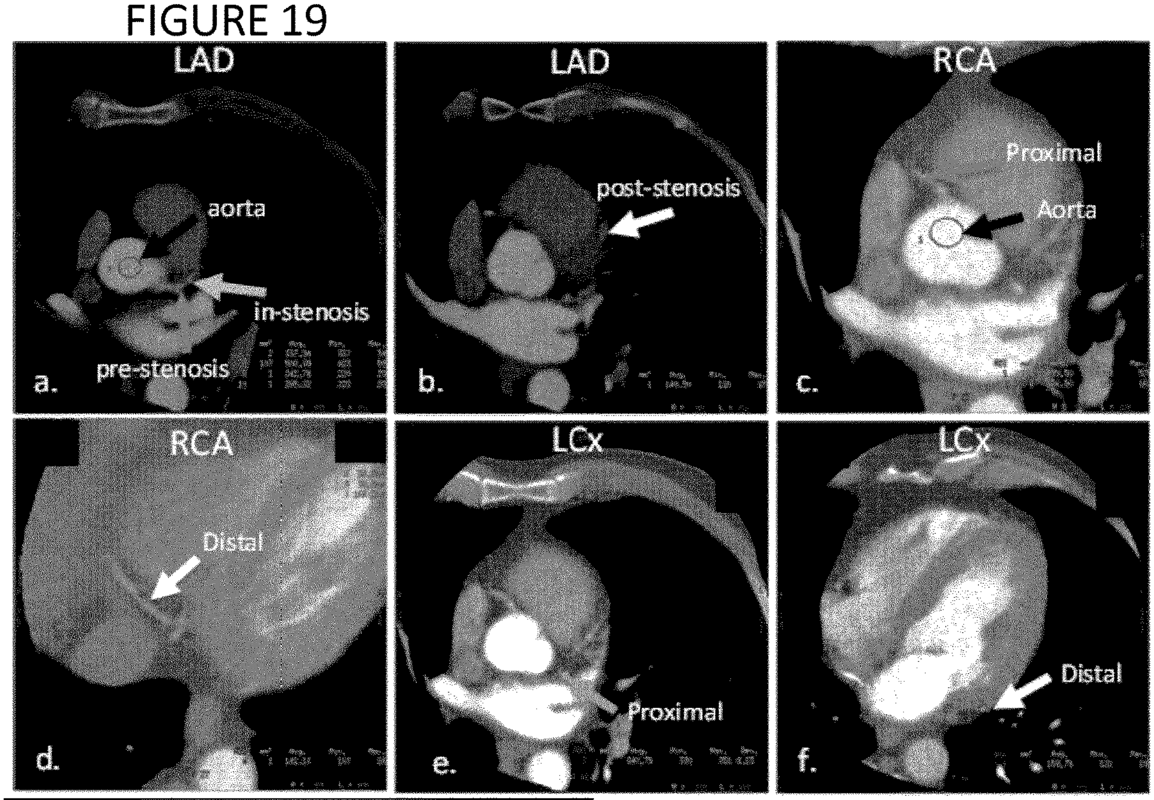
FIG. 19 shows contrast-enhanced heart images of patient #3 at the slices where the time-enhancement curves in the LAD (a. pre-stenosis and in-stenosis; b. post-stenosis) and RCA (c. proximal; d. distal) and LCx (e. proximal; f. distal) were measured.
Figure 20:
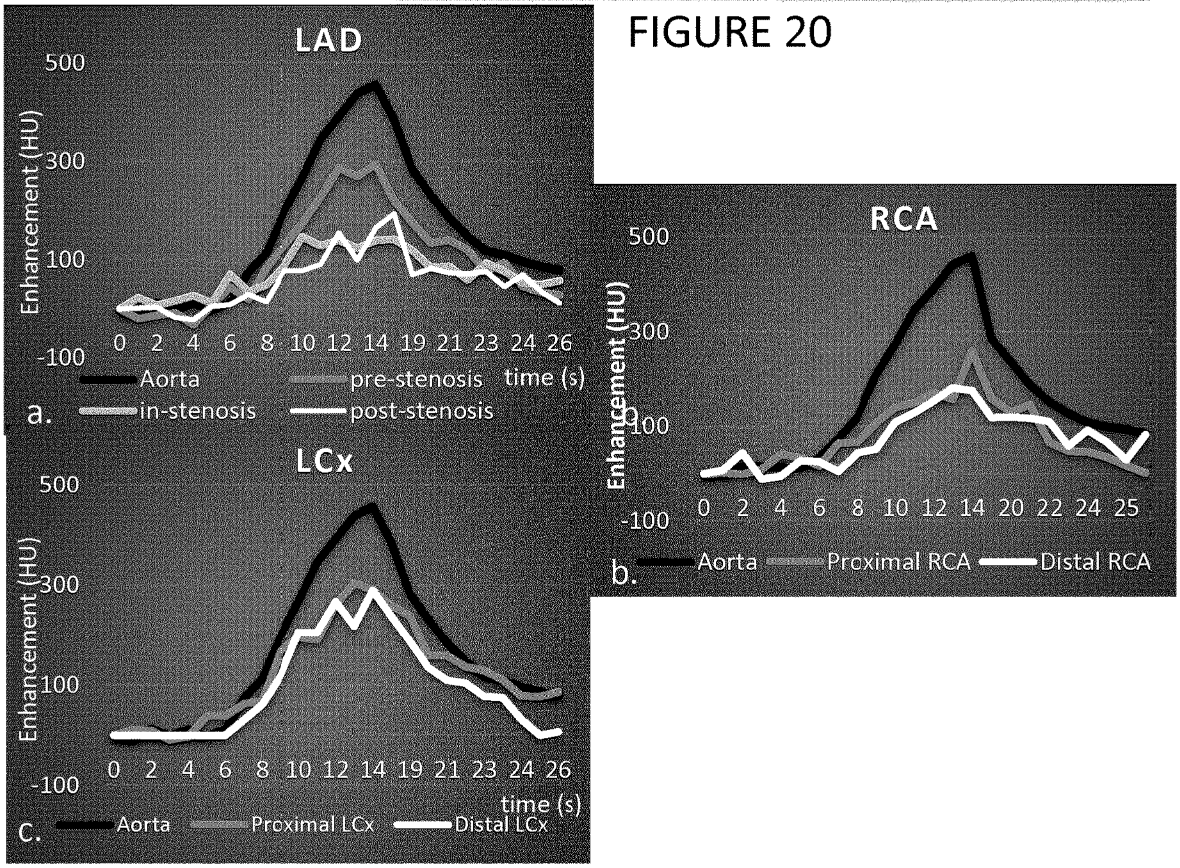
FIG. 20 shows a comparison of the time-enhancement curves measured in the (a) left anterior descending (LAD), (b) right coronary (RCA) and (c) left circumflex (LCx) arteries of patient #3.
Figure 21:
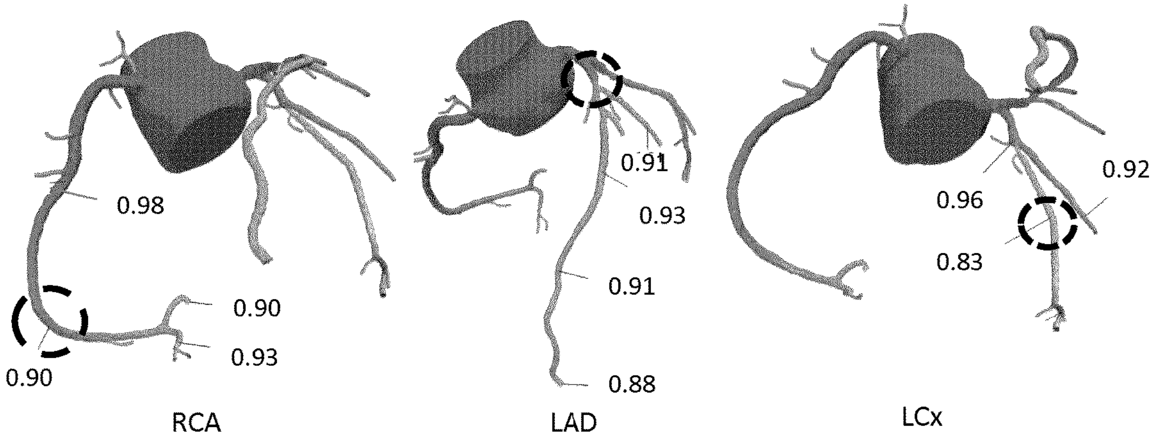
FIG. 21 shows FFR-CT maps of the three coronary arteries for patient #3; the coronary segments where FFR measurement was taken with the proposed dynamic angiographic method are highlighted by the dotted circles.

(b) Figures. FIGS. 19*a* and 19*b* show the contrast-enhanced heart images at one axial slice location. The ROI where the aortic and LAD TECs were measured are shown. The two axial slices were 10 mm apart. FIGS. 19*c* and 19*d* show the axial slices where the proximal and distal RCA TECs were measured. Similarly, FIGS. 19*c* and 19*f* show the slices where the proximal and distal LCx TECs were measured. FIG. 20*a*-20*c* show the TECs measured from the LAD, RCA and LCx, respectively. The aortic TEC was also shown in each graph for comparison. FIG. 21 shows the FFR-CT maps for each coronary artery. The dotted circle in each map denotes the approximate location where the FFR measurement was taken with our dynamic angiographic method. FIG. 22*a* shows the curve-reformatted view of the LAD. FIG. 22*b* shows the material decomposition of the plaque in the LAD using a CT number based segmentation. FIG. 22*c* shows the cross-sectional view of the LAD with the plaque decomposed into different materials as in FIG. 22*b*. FIGS. 22*d* and 22*e* show the reformatted lumen view of the LAD with the diameter of the pre-, in- and post-stenosis segments labelled. It was clear that the luminal narrowing in the proximal segment was over 50%.

(c) Results. Findings from patient #3 relating to blood flow rate, blood flow pressure and FFR calculations are summarized in Table 4.

TABLE 4

| Summary of physiological measurements in the LAD (stenosed), RCA (non-stenosed) and LCx (non-stenosed) of patient #3. | | | | | | | |
|---|---|---|---|---|---|---|---|
| | Lumen diameter (cm) | Coronary blood flow (mL/min) | Degree of stenosis (% lumen narrowing) | Reynolds number | Turbulent flow | Pressure drop from ROI 1 (ΔP, mmHg) | Fractional flow reserve (FFR) |
| Pre-sten LAD | 0.35 | 396.55 | — | 841.5 | N | — | — |
| In-sten LAD | 0.05 | 483.06 | >50% | 146.4 | N | −12.6 | 0.89 |
| Post-sten LAD | 0.21 | 600.78 | — | 2124.8 | Probably | −44.5 | 0.64 |
| Proximal RCA | 0.33 | 463.92 | — | — | — | — | — |

TABLE 4-continued

Summary of physiological measurements in the LAD (stenosed), RCA (non-stenosed) and LCx (non-stenosed) of patient #3.

| | Lumen diameter (cm) | Coronary blood flow (mL/min) | Degree of stenosis (% lumen narrowing) | Reynolds number | Turbulent flow | Pressure drop from ROI 1 (ΔP, mmHg) | Fractional flow reserve (FFR) |
|---|---|---|---|---|---|---|---|
| Distal RCA | 0.26 | 509.28 | — | 1846.5 | N | −9.0 | 0.93 |
| Proximal LCx | 0.32 | 337.02 | — | 793.3 | N | — | — |
| Distal LCx | 0.23 | 435.89 | — | 1407.6 | N | −19.3 | 0.84 |

(i) RCA. CCTA revealed no stenosis in the RCA. The proximal and distal segments of the RCA shown in FIGS. 19*c* and 19*d* were 6.0 cm apart. The coronary blood flow in the proximal and distal RCA were 463.9 mL/min and 509.3 mL/min respectively. The pressure difference between the two segments was-9.0 mmHg. The FFR derived from our method was 0.93, which was very close to the FFR value estimated with FFR-CT (0.96).

(ii) LCx. CCTA showed that the LCx had no stenosis. The proximal and distal segments of the LCx shown in FIGS. 19*e* and 19*f* were 5.35 cm apart. The coronary blood flow in the proximal and distal LCx segments were 337.0 mL/min and 435.9 mL/min respectively. The flow pressure difference between the two segments was-19.26 mmHg. The corresponding FFR derived from our method was 0.84, which was almost identical to the FFR value estimated with FFR-CT (0.83).

Figure 22:
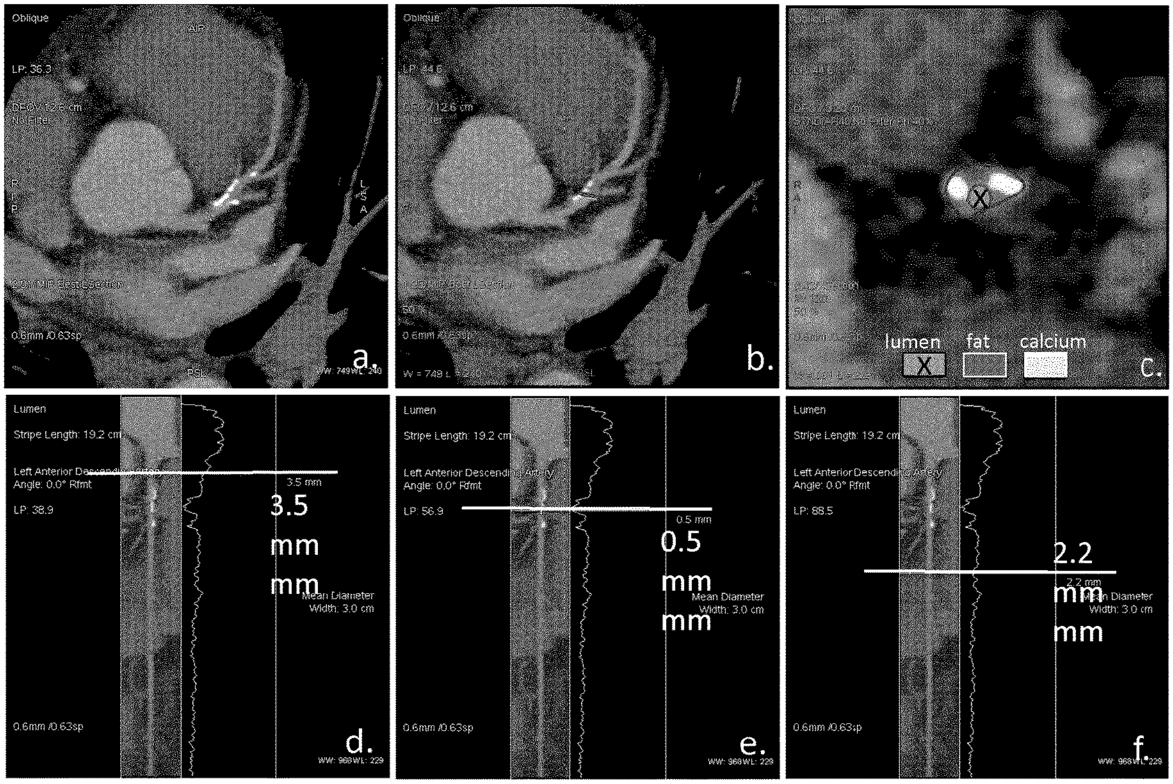
FIG. 22 shows ((a) and (b)) curve-reformatted view of the LAD with the plaque composition shown; (c) cross-sectional view of the LAD with the plaque composition shown; ((d) to (f)) reformatted lumen view of the LAD with the location of the pre-stenosis, in-stenosis and post-stenosis segments and the corresponding lumen diameters shown.

(iii) LAD. CCTA revealed a long calcified and fatty plaque in the proximal segment of the LAD that resulted in a >50% lumen narrowing (FIG. 22). The AUC in the in-stenosis and post-stenosis segments was considerably lower compared to the AUC in the pre-stenosis segment (FIG. 20*a*), which was in contrast to the other two non-stenosed arteries where there was minimal difference in the AUC between the proximal and distal coronary segments (FIG. 20*b/c*). The coronary blood flow in the pre-stenosis, in-stenosis and post-stenosis LAD segments were 396.6 mL/min, 483.1 mL/min and 600.8 mL/min respectively. The total pressure loss across the stenosis due to friction and turbulence was-44.5 mmHg (estimated from Eq. 4, 5 and 10). Given the patient's systolic pressure during adenosine stress was 124 mmHg ($P_A$), $P_B$ equals 79.5 mmHg and hence the FFR was equal to 0.64. The FFR measurement with our dynamic angiographic imaging method was in disagreement with the FFR-CT finding, which concluded that the stenosed LAD had a normal FFR value (~0.91). Both the SPECT and CT myocardial perfusion measurement revealed ischemia in the myocardium. Specifically, the CT perfusion measurement showed that the mean hyperemic myocardial perfusion in the LAD territory was 166.1 ml/min/100 g, which was much lower than the mean hyperemic myocardial perfusion in non-ischemic myocardium in 21 CAD patients (215.1 ml/min/100 g, results from our recent single-center study that was presented at the RSNA scientific meeting in November 2017).

In addition to blood flow and pressure, other flow characteristics were also derived. For example, using mathematical methods described in Example 4 from FIG. 8, the shear stress in the pre-stenosis, in-stenosis and post-stenosis segments of the LAD were estimated to be 0.047, 19.68 and 0.33 kPa respectively. Furthermore, the area under the curve (AUC) for the pre-stenosis, in-stenosis and post-stenosis segments of the LAD were 2592.79, 2128.44 and 1711.38 HU·s respectively; The corresponding peak contrast enhancement in the same segments were 254.1, 146.1 and 193.2 HU respectively; The corresponding rate of change of the AUC in these segments in the wash-in phase were 20.2, 8.7 and 8.3 HU·s respectively.

(d) Interpretation. As shown in a recent systematic review by Cook et al (2017; JAMA Cardiology, Vol 2 (7): 803-810), the CT-based FFR measurement agrees well with the catheter-based FFR measurement when the degree of stenosis is minimal or absent. Patient #3 had a non-stenosed RCA and a non-stenosed LCx, so we can use the FFR-CT assessment in these normal arteries as the reference to compare with the FFR measurement with our method. Our results showed that our method agreed extremely well with FFR-CT in these normal (non-stenosed) arteries. However, there was a noticeable difference between our method and FFR-CT in the stenosed LAD. While FFR-CT suggested the stenosis was not functionally significant (FFR>0.80), the assessment with our method suggested that this lesion was indeed obstructive (FFR<0.80). Our findings are in agreement with the SPECT and CT myocardial perfusion measurement, both of which showed ischemia in the myocardium. Additionally, the AUC in the in-stenosis and post-stenosis segments was substantially smaller compared to the AUC in the pre-stenosis segment, further suggesting the existence of a large pressure drop across the stenosis. The findings in this study suggest that the dynamic angiographic imaging method provided herein may be more reliable compared to FFR-CT for the assessment of intermediately stenosed coronary arteries.

Our finding also revealed that the in-stenosis segment of the LAD exhibited the largest shear stress compared to the adjacent segments that are less narrowed. The ability of our method for assessing the shear stress opens a new window of opportunity for a more accurate assessment of the risk of plaque rupture (thrombosis), which depends on plaque morphology, composition and magnitude of shear force exerted to the plaque. Our results also showed that other flow characteristics such as the rate of change of AUC and peak contrast enhancement can be derived from the same set of images that may be useful to differentiate between stenosed and non-stenosed arteries.

Experimental Exemplification: Experimental Example 4. The results of Experimental Example 4 are related to the use of mathematical methods described for Complement Step 1 from FIG. 8.

Figure 23:
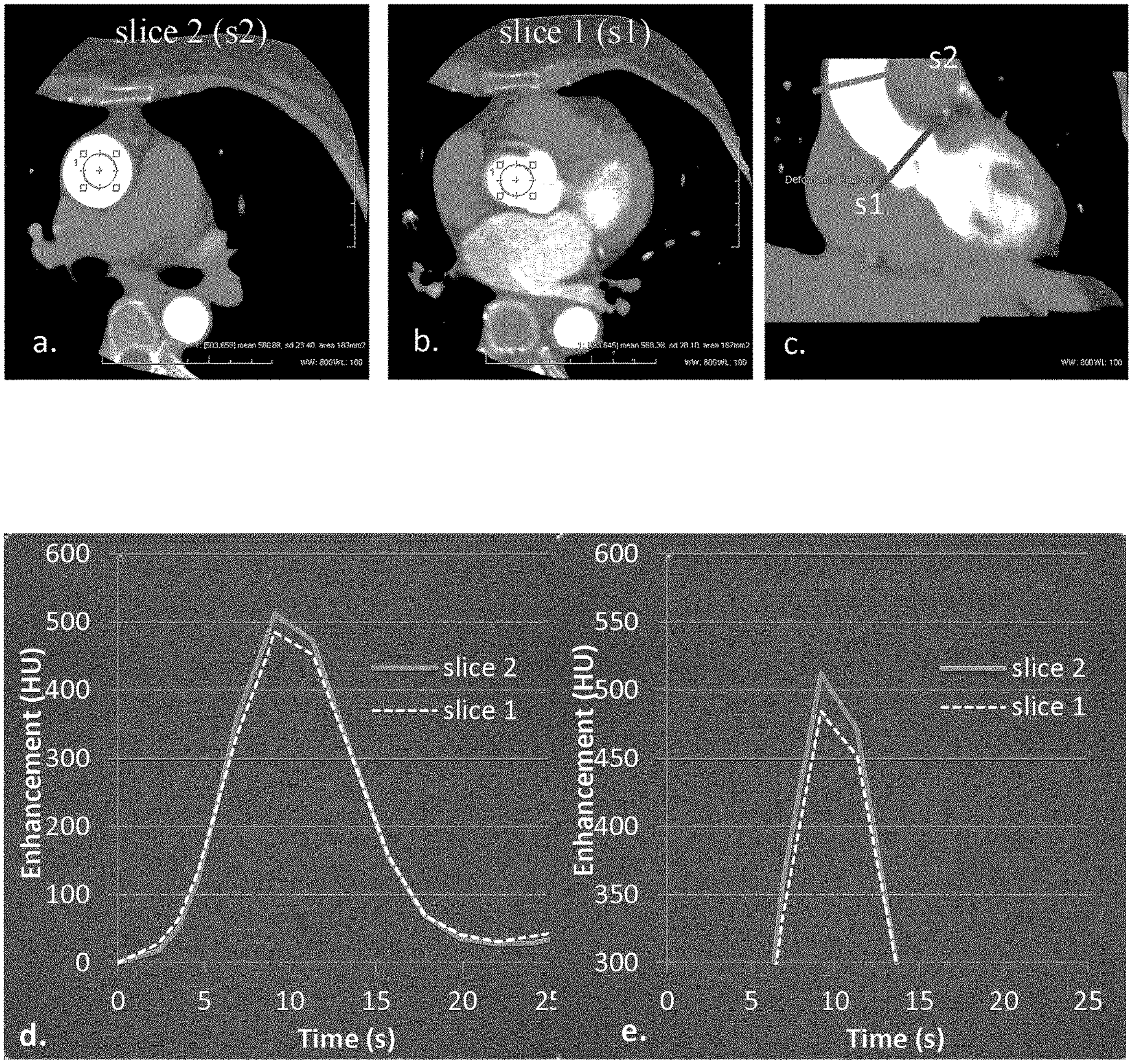
FIG. 23 shows ((a) and (b)) two slices of contrast-enhanced images from patient #1; (c) location of the two slices within the ascending aorta; ((d) and (e)) comparison of time-enhancement curve measured at the two different slices in the ascending aorta.

FIGS. 23*a* and 23*b* shows the two slices of contrast-enhancement heart images where the aortic time-enhancement curve was measured for patient #1 (same patient as in Experimental Example 1). The distance between the two slices was about 3.5 cm (FIG. 23*c*). Slice 1 was just above the orifice of the ascending aorta. The orifices of the left and right coronary arteries were located between slice 1 and 2

(not shown in this reformatted view of the heart). FIG. 23*d* shows the time-enhancement curves measured at slice 1 and 2. FIG. 23*e* provides a magnified scale to show these curves around their peak values. The area under curve (AUC) at slice 1 and 2 was 4316.75 and 4573.37 HU respectively. The AUC at slice 1 was 5.6% smaller than the AUC at slice 2. The result is comparable to the expected value (~5%) as explained in Mathematical Analysis of Complement Step 1 described above, which indicated that Complement Step 1 can be used to estimate the fraction of tracers going to the coronary system from the aorta.

Experimental Exemplification: Experimental Example 5. The results of Experimental Example 5 are related to the use of mathematical methods described for Complement Step 2 from FIG. 8.

Figure 24:
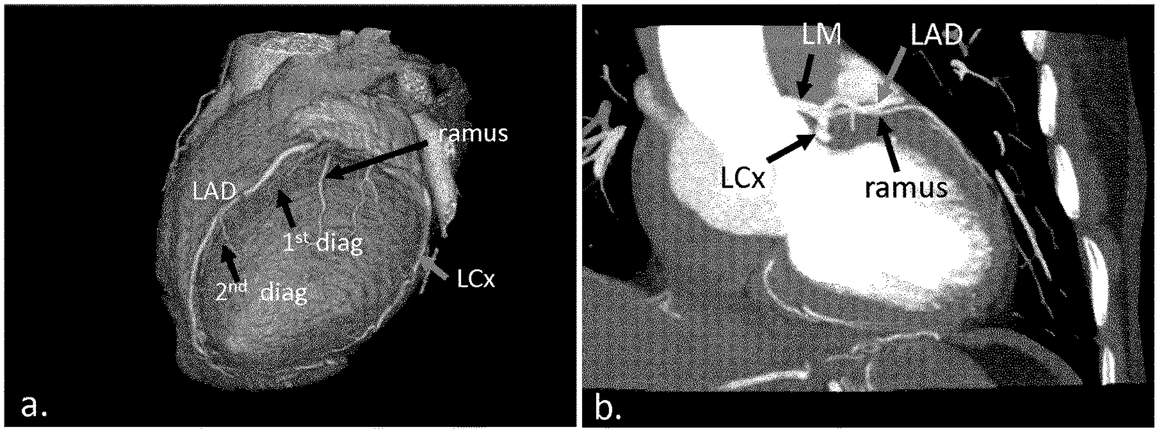
FIG. 24 shows left coronary arteries of patient #2 as shown in (a) three-dimensional rendered and (b) curve reformatted image of the heart.

FIGS. 24*a* and 24*b* show the left coronary arteries of patient #2 (same patient as in Experimental Example 2). Usually, the LM bifurcates into the LCx and LAD only, but the LM of this patient trifurcates into the intermediate branch (ramus) in addition to the LCx and LAD. The radius of each vessel and the corresponding maximum contrast enhancement are provided in Table 5. According to Eq. (20) and (21), the product of radius squared and maximum contrast enhancement (values in the second last column in Table 5) of the parent vessel (LM) should equal the sum of the product of each daughter vessel (LCx, LAD and Ramus). Our finding showed that this is the case—there was only a 2.85% difference between these values (4890.73 vs. 5032.29). The subtle difference between these values could be attributed to image noise and residual motion in the coronary arteries. The percentage of tracers distributed to each daughter vessel (LCx, LAD and Ramus) from the parent vessel (LM) was estimated to be 54.2%, 36.5% and 12.2% respectively. The findings confirm the validity of Eq. (20) and (21), which provide a reliable way to estimate the mass of tracers in each coronary artery.

TABLE 5

Summary of radius and maximum contrast enhancement and fraction of tracers in each left coronary artery of patient #2.

| Coronary artery | Radius (r, cm) | $r^2$ | Max enhancement (HU) | $(r^2)$ · (max HU) | Fraction of tracers |
|---|---|---|---|---|---|
| LM | 4.7 | 22.09 | 221.4 | 4890.73 | 1.000 |
| Proximal LCx | 3.7 | 13.69 | 193.6 | 2650.38 | 0.542 |
| Proximal LAD | 3.1 | 9.61 | 185.8 | 1785.54 | 0.365 |
| Ramus | 1.9 | 3.61 | 165.2 | 596.37 | 0.122 |

Experimental Exemplification: Experimental Example 6. The results of Experimental Example 6 illustrate use of time-enhancement curves to assess blood flow without requiring mathematical methods described in Examples 1-4 from FIG. 8, compare non-hyperemic versus hyperemic stress during scan acquisition, and illustrate additional metrics (i.e., in addition to those shown in FIG. 8) derived from time-enhancement curve for functional assessment of blood flow.

Patient information. Patient #4 was a 78 year old male who had a triple-vessel coronary artery disease (CAD). The physiological condition in each coronary artery was different at the time of the imaging study. This study serves to demonstrate the advantages of DAI in the following aspects:

1. functional assessment of CAD in presence of blooming artifacts arising from calcified plaque and metal stent in the coronary lumen;
2. functional assessment of CAD in presence of multi-vessel lesions;
3. more than one metric can be derived from the coronary time-enhancement curves, in addition to coronary blood flow, shear stress and fractional flow reserve (FFR), that may be useful for functional assessment of coronary artery stenosis. These metric include peak enhancement (PE), area under the curve (AUC), upslope and downslope, skewness and kurtosis, of a time-enhancement curve;
4. the metrics described in (3) measured at rest may be sufficient for functional CAD assessment, implying that hyperemic stress of the patient with drug may not be required.

Figure 25:
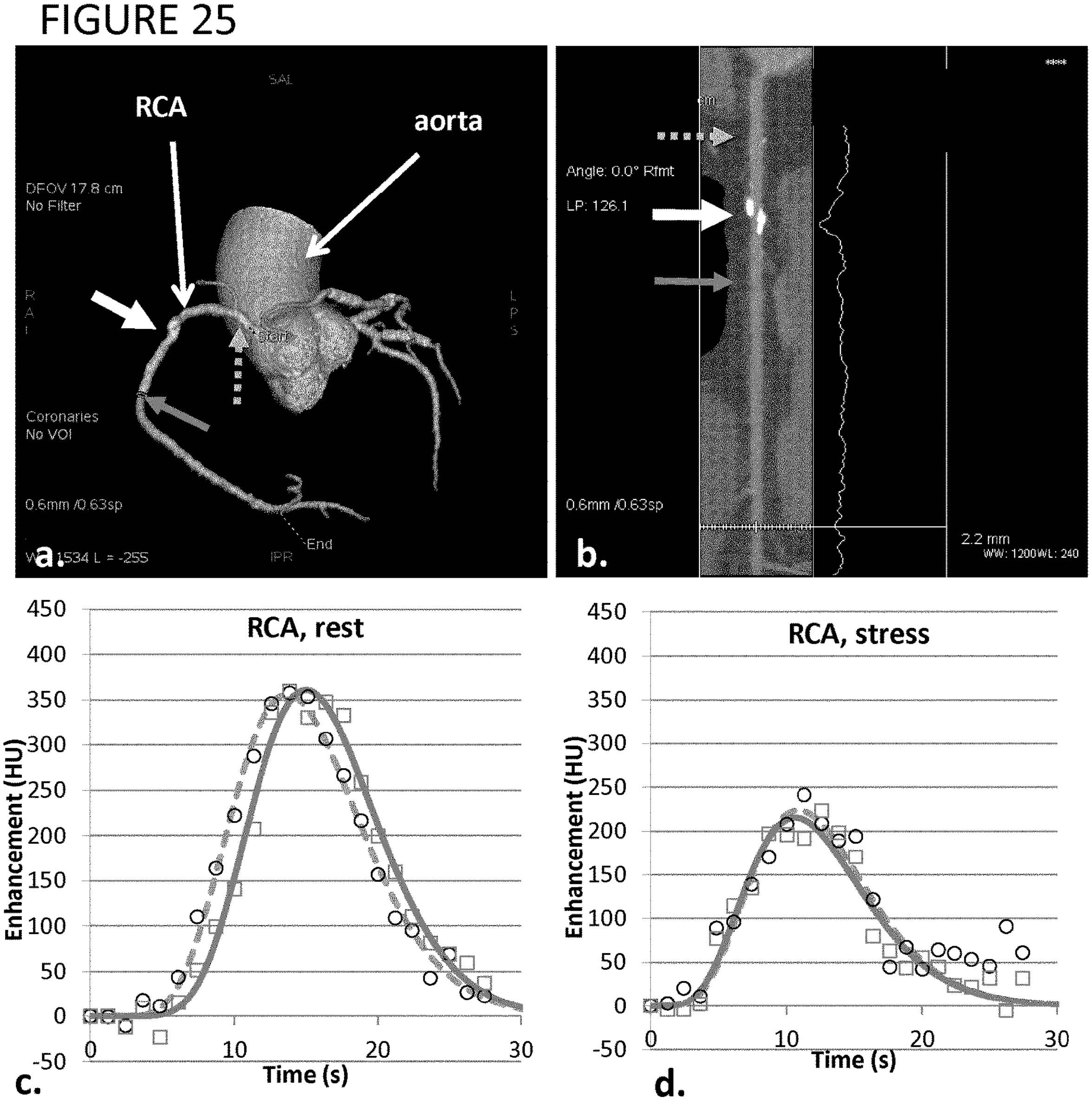
FIG. 25 shows ((a) and (b)) a plaque obstruction in RCA for patient #4, and pre- and post-plaque time-enhancement curves generated from scan data acquired during (c) non-hyperemic or rest condition and (d) hyperemic stress condition.

FIG. 25 shows the right coronary artery (RCA) with two calcified plaques close to each other in the proximal segment (white arrows in (a) and (b)). The calcium on each side within the lumen affects the measurement of the lumen diameter, which is the information required for the current FFR-CT methods that are based on computational fluid dynamics. The dotted light-grey arrows and the solid dark-grey arrows in (a) and (b) show the locations at which the pre-plaque (upstream) and post-plaque (downstream) time-enhancement curves were sampled. In the graphs shown in (c) and (d), the circles represent the measured enhancement at different time points in the pre-plaque position at rest and during maximal vasodilatory stress, respectively. The dotted light-grey curves in these graphs represent the corresponding fitted time-enhancement curves. Similarly, the squares in (c) and (d) are the measured enhancement at different time points in the post-plaque position at rest and stress, respectively. The corresponding fitted time-enhancement curves are shown as the solid dark-grey curves in these graphs.

Our results show that the time-enhancement curves upstream and downstream of the calcified plaques were almost identical to each other at both the rest and stress conditions. This is evident by the indifferent PE (peak enhancement) and AUC (area under the curve) between the two curves at each condition. Furthermore, the pre- and post-plaque AUC at stress was substantially reduced compared to those at rest. AUC is inversely proportional to the coronary blood flow. This means the coronary blood flow in the RCA increased considerably at the pre-plaque and post-plaque locations at stress from the baseline (rest), and the magnitude of blood flow increase was consistent between the pre-plaque and post-plaque locations. Hence, the finding suggests the plaque was not functionally significant.

Figure 26:
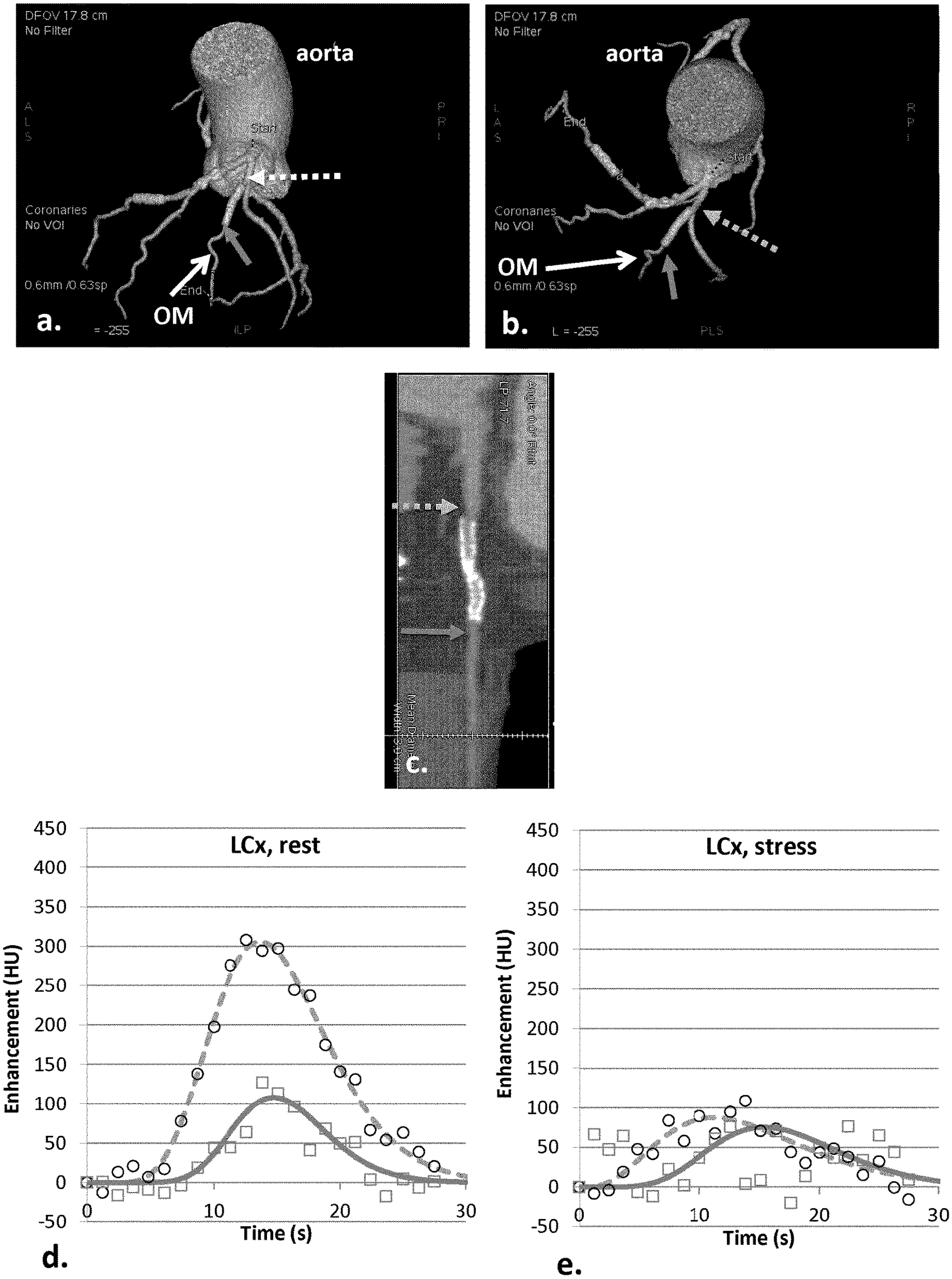
FIG. 26 shows ((a), (b) and (c)) a stent obstruction in LCx for patient #4, and pre- and post-stent time-enhancement curves generated from scan data acquired during (d) non-hyperemic or rest condition and (e) hyperemic stress condition.

The obtuse marginal (OM) branch of the left circumflex (LCx) artery shown in FIG. 26 had an implanted stent in the proximal segment. The time-enhancement curves measured upstream (dotted light-grey arrows in (a) to (c)) and downstream (solid dark-grey arrows in (a) to (c)) to the stent are shown in the graphs in (d) and (c). The reformatted view of the OM artery (c) shows that the lumen visualization was significantly affected by the blooming artifacts, with the middle part of the stent seen to be completely blocked. However, the time-enhancement curve acquired after (downstream) the stent at rest (dark-grey plot with square markers in (d)) shows that the stented lumen was narrowed but not completely blocked because there was passage of contrast at that sampling site. At rest, the post-stent AUC was considerably smaller compared to the pre-stent AUC, indicating that the coronary blood flow after the stent was faster than before the stent due to a narrower stented lumen as depicted by the Bernoulli's equation.

The pre-stent AUC at stress (dotted light-grey plot with circle markers in (c)) was much smaller compared to the pre-stent AUC at rest (dotted light-grey plot in (d)), while the post-stent AUC at stress (solid dark-grey plot with square markers in (c)) was minimally reduced from that at rest (solid dark-grey plot in (d)). The finding shows that there was a large increase in coronary blood flow in the segment prior to the stent at stress due to maximal vasodilation, but the increase in blood flow after the stent was minimal due to absence of or minimal vasodilation. It is therefore possible that the stenosis within the stent was functionally significant.

Figure 27:
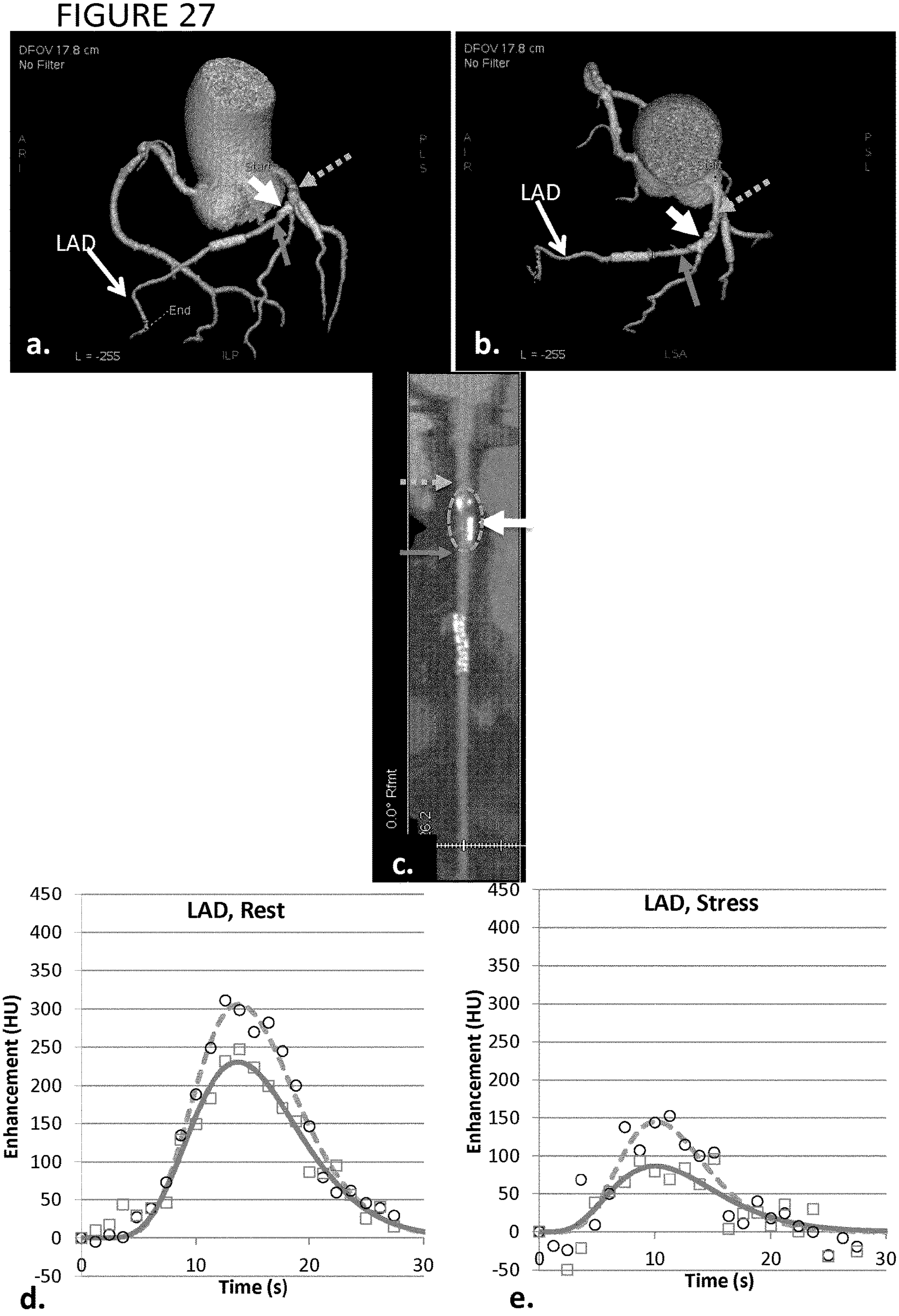
FIG. 27 shows ((a), (b) and (c)) a plaque obstruction in LAD for patient #4, and pre- and post-plaque time-enhancement curves generated from scan data acquired during (d) non-hyperemic or rest condition and (e) hyperemic stress condition.

The left anterior descending artery (LAD) shown in FIG. 27 had multiple lesions. The proximal segment had complex calcified and non-calcified plaques (white arrows in (a) to (c); the middle segment had a stent implanted. The dotted light-grey and solid dark-grey arrows in (a) to (c) denote the locations where the pre-plaque and post-plaque time-enhancement curves were measured. The pre-(circle markers) and post-plaque (square markers) time-enhancement curves measured at rest and stress are shown in (d) and (c), respectively.

The results show a moderate decrease in the AUC of the post-plaque curve relative to the pre-plaque curve, at both the rest and stress conditions. Compared to the plaque in the RCA (FIG. 25) which was not functionally significant, the plaque in the proximal LAD resulted in a larger degree of lumen narrowing as reflected by a larger decrease in the AUC across the plaque at rest. However, by comparing the LAD post-plaque curve between the rest and stress conditions, we confirmed there was considerable increase in coronary blood flow at stress, suggesting the plaque in the proximal LAD may not be as functionally significant as the stenosed stent in the LCx (FIG. 26), which showed minimal increase in blood flow at stress in the segment below the stent.

Metrics of blood flow, flow pressure, FFR and shear stress have been exemplified in Experimental Examples 1-3. Additional metrics derived from time-enhancement curves can be used for functional assessment of coronary stenosis. The time-enhancement curves shown in FIGS. 25 and 26 can be used to illustrate the additional metrics. We first review the time-enhancement curves in the RCA acquired before and after the plaque (FIG. 25). As discussed above, these two curves are very similar to each other, indicating the lumen narrowing in between the two sites was minimal. The appearance of a time-enhancement curve can be quantitatively described using the following examples of additional metrics: area under curve (AUC), peak enhancement (PE), upslope, downslope, skewness, kurtosis. Skewness describes the asymmetry of the curve and its value ranges from −1 to +1. A zero skewness means the curve is perfectly symmetrical on both sides (upslope side compared to downslope side). A negative skewness implies the curve has a longer tail on the left (upslope) side than the right (downslope) side, whereas a positive skewness means the curve has a longer tail on the right (downslope) side than the left (upslope) side. By contrast kurtosis describes the sharpness of the curve. The normal value of kurtosis is 3. If the kurtosis is less than 3, the curve is flatter than normal, whereas a kurtosis greater than 3 implies the curve has a higher peak than normal. Table 6 summarizes the metrics for the RCA pre- and post-plaque curves at rest. The difference in each metric between the pre- and post-plaque curves is given by the subtraction of the two metrics (post-pre) and the ratio of the two metrics (post divided by pre).

TABLE 6

| REST | AUC (HU · s) | PE (HU) | Upslope (HU/s) | Downslope (HU/s) | Skewness | Kurtosis |
|---|---|---|---|---|---|---|
| RCA pre-plaque | 4047.51 | 355.49 | 52.74 | −36.57 | 0.595 | −1.211 |
| RCA post-plaque | 3982.01 | 361.00 | 49.93 | −36.01 | 0.634 | −1.163 |
| Difference | −65.5 | 5.51 | −2.81 | 0.558 | 0.039 | 0.048 |
| Ratio | 0.984 | 1.015 | 0.947 | 0.985 | 1.066 | 0.960 |

The same metrics for the RCA pre- and post-plaque curves at stress are summarized in Table 7:

TABLE 7

| STRESS | AUC (HU · s) | PE (HU) | Upslope (HU/s) | Downslope (HU/s) | Skewness | Kurtosis |
|---|---|---|---|---|---|---|
| RCA pre-plaque | 2452.44 | 224.03 | 17.33 | −18.23 | 0.660 | −1.129 |
| RCA post-plaque | 2369.71 | 214.68 | 13.98 | −16.84 | 0.653 | −1.138 |
| Difference | −82.73 | −9.35 | −3.35 | 1.384 | −0.007 | −0.009 |
| Ratio | 0.966 | 0.958 | 0.807 | 0.924 | 0.989 | 1.008 |

The same metrics for the pre- and post-stent curves in the OM branch of the LCx artery at rest are shown in Table 8:

TABLE 8

| REST | AUC (HU · s) | PE (HU) | Upslope (HU/s) | Downslope (HU/s) | Skewness | Kurtosis |
|---|---|---|---|---|---|---|
| LCx pre-stent | 3524.68 | 303.33 | 44.83 | −30.89 | 0.571 | −1.238 |

TABLE 8-continued

| REST | AUC (HU · s) | PE (HU) | Upslope (HU/s) | Downslope (HU/s) | Skewness | Kurtosis |
|---|---|---|---|---|---|---|
| LCx post-stent | 999.25 | 107.78 | 14.96 | −13.49 | 0.903 | −0.736 |
| Difference | −2525.43 | −195.55 | −29.87 | 17.41 | 0.332 | 0.502 |
| Ratio | 0.284 | 0.353 | 0.334 | 0.437 | 1.581 | 0.595 |

The same metrics for the pre- and post-stent curves in the OM branch of the LCx artery at stress are provided in Table 9:

TABLE 9

| STRESS | AUC (HU · s) | PE (HU) | Upslope (HU/s) | Downslope (HU/s) | Skewness | Kurtosis |
|---|---|---|---|---|---|---|
| LCx pre-stent | 1311.12 | 87.57 | 4.886 | −6.247 | 0.171 | −1.452 |
| LCx post-stent | 1001.44 | 75.10 | 9.840 | −5.241 | 0.308 | −1.427 |
| Difference | −309.68 | −12.47 | 4.954 | 1.006 | 0.137 | 0.025 |
| Ratio | 0.764 | 0.868 | 2.014 | 0.839 | 1.801 | 0.983 |

It is clear that the RCA pre- and post-plaque curves were not substantially different from each other as reflected by their comparable AUC, PE, slope, skewness and kurtosis in both the rest and stress conditions (the ratio associated to each metric was close to unity at both the rest and stress states). Furthermore, the RCA curves at stress had lower AUC/PE/slope but similar skewness/kurtosis compared to the RCA curves at rest, suggesting that the change in coronary time-enhancement curve across the plaque in the proximal RCA at stress was mainly due to the higher flow rate during maximal vasodilation as the curve was not significantly distorted due to complex lumen narrowing. By contrast, the LCx pre- and post-stent curves were very different from each other, as reflected by the larger differences in the metrics and the corresponding ratios exhibited greater differences from unity. The results indicate that the coronary time-enhancement curve was substantially distorted by the lumen narrowing within the stent.

In summary, the examples shown in FIG. 25 (RCA plaque) and FIG. 26 (LCx stent) suggest that metrics in addition to those of coronary blood flow, FFR and shear stress, can be derived from the coronary time-enhancement curves. These additional metrics acquired at the rest and stress physiological states can be used individually or in combination for functional evaluation of a coronary artery lesion.

Experimental Exemplification: Experimental Example 7. The results of Experimental Example 7 illustrate accommodation of imaging modalities other than CT in the DAI method and system. More specifically, Example 7 shows the DAI method and system incorporating invasive coronary angiography as the imaging technology.

Figure 28:
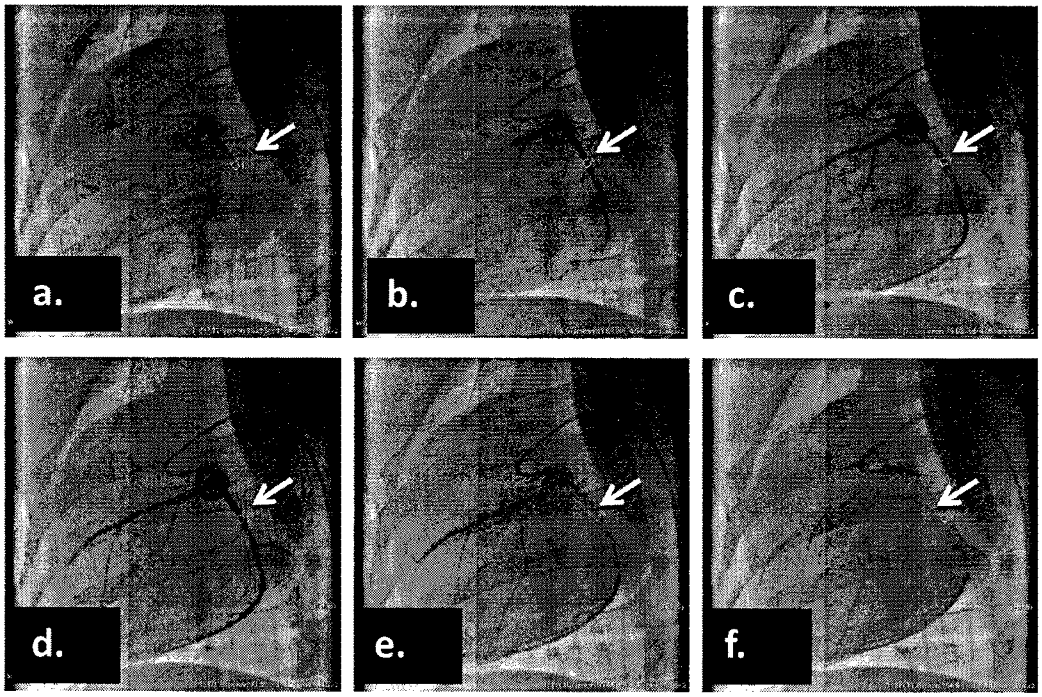
FIG. 28 shows ((a) to (f)) time-ordered images of LAD of a pig acquired using invasive coronary angiography, and plots of (g) contrast signal intensity versus frame number and (h) time-enhancement curve.
Figure 28:
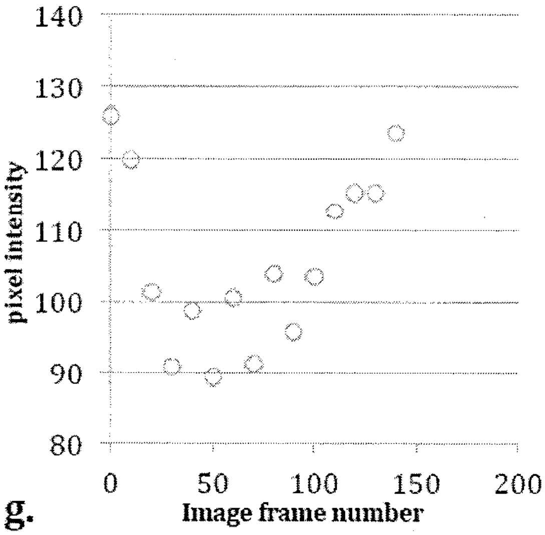
Figure 28:
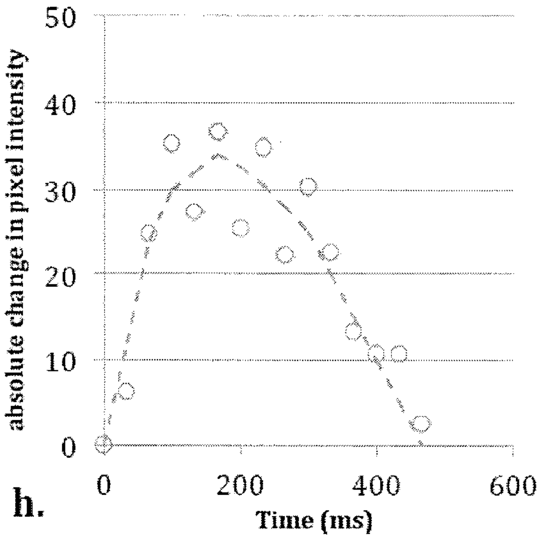

Compared to contrast-enhanced CT, one difference in invasive coronary angiography is that bolus of x-ray dye (iodinated contrast agent) is directly injected into the left or right coronary arteries at the orifice via a catheter (selective angiography) rather than intravenous injection. The passage of contrast solution in an artery leads to decrease in signal intensity in the blood vessel (the x-ray dye appears as dark colour as opposed to bright colour in a CT angiographic or CT perfusion source image). In FIG. 28, the first-pass of contrast agent in the LAD artery is shown in (a) to (f). To obtain a coronary time-enhancement curve similar to other previous examples, we first measure the pixel intensity in the motion-corrected coronary artery at different image frames covering the period from before contrast wash-in to after contrast wash-out. The measured pixel intensity values at the sampling site denoted by the white arrows in (a) to (f) are shown in (g). We then calculate the absolute change in pixel intensity relative to the first time point when there is no contrast in the artery, and convert the number of image frames to time using the image acquisition rate applied in coronary angiography. In this study, the images were acquired at 30 frames per second. We can now convert the plot in (g) to the plot in (h), with the y-axis in absolute change in pixel intensity (contrast enhancement), and the x-axis in time. The dashed line in (h) represents the fitted curve to the measured data.

We also need to know the total mass of tracers injected into the artery as described previously. In this study, 10 mL of contrast at a concentration of 270 mgI/mL was injected at the orifice, and about 3 mL of contrast entered into the ascending aorta and did not enter into the left coronary arteries (i.e. about 7 mL of contrast in the left coronary arteries). We also need to know the conversion factor between the unit increase in pixel intensity and the concentration of contrast in coronary angiography, which can be determined from phantom experiments. With all the information, we can derive coronary blood flow, FFR and other metrics shown in previous Experimental Examples.

Figure 29:
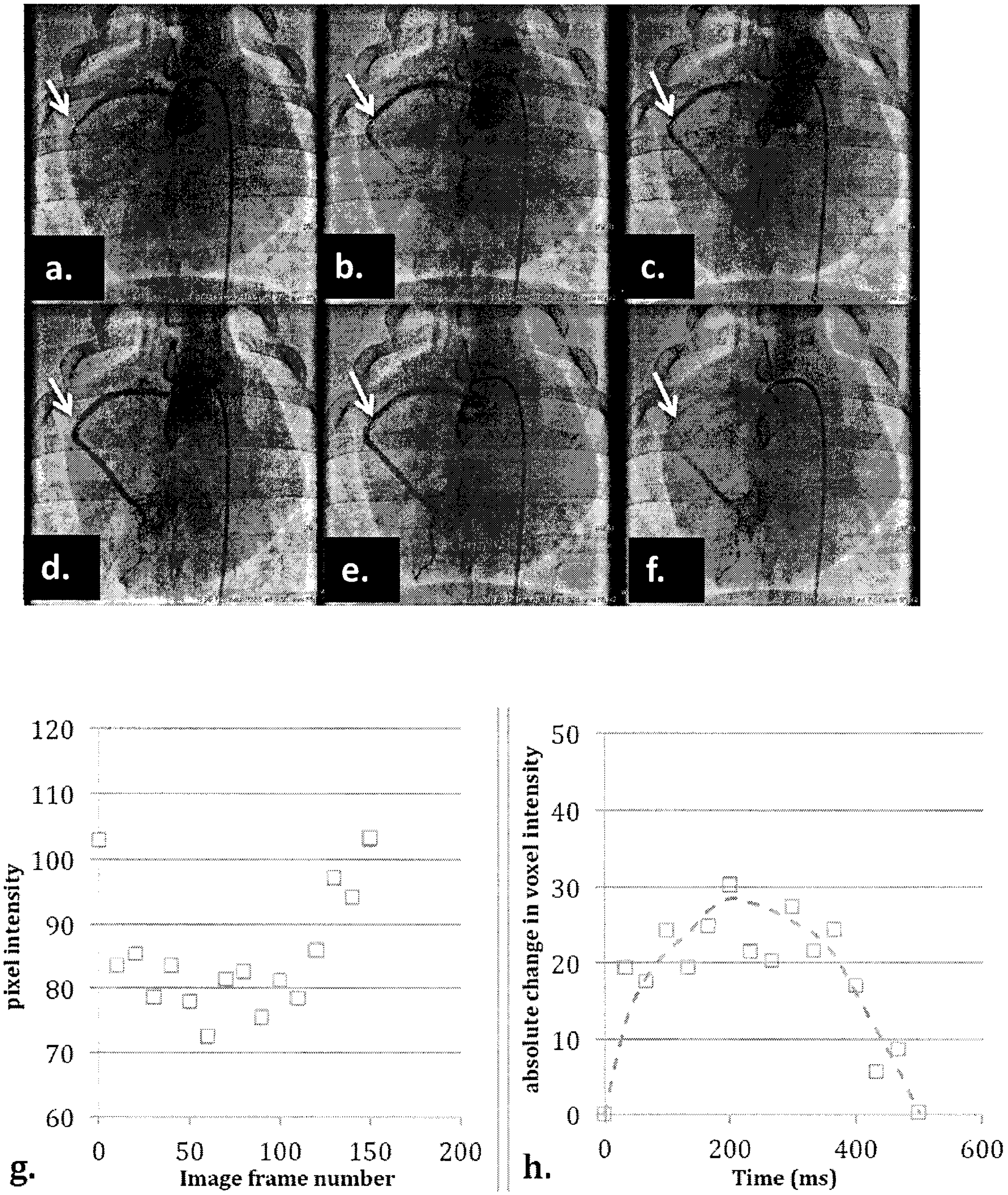
FIG. 29 shows ((a) to (f)) time-ordered images of RCA of a pig acquired using invasive coronary angiography, and plots of (g) contrast signal intensity versus frame number and (h) time-enhancement curve.

FIG. 29 shows another example acquired from the same pig as shown in FIG. 28 to illustrate the proposed method can be applied to any artery of interest in selective coronary angiography. In this study, contrast agent was injected directly into the right coronary artery (RCA) at the orifice. Images in (a) to (f) show the first pass circulation of contrast in the RCA over a short period of time. The data in (g) shows the pixel intensities measured from the motion-corrected RCA at the sampling site denoted by the white arrows in (a) to (f), and the corresponding coronary time-enhancement curve is shown as the dotted line in (h).

Experimental Exemplification: Experimental Example 8. The results of Experimental Example 8 illustrate accommodation of imaging modalities other than CT in the DAI method and system. More specifically, Example 8 shows the DAI method and system incorporating MRI as the imaging technology. Gadolinium-based T1-weighted MR myocardial perfusion imaging.

Figure 30:
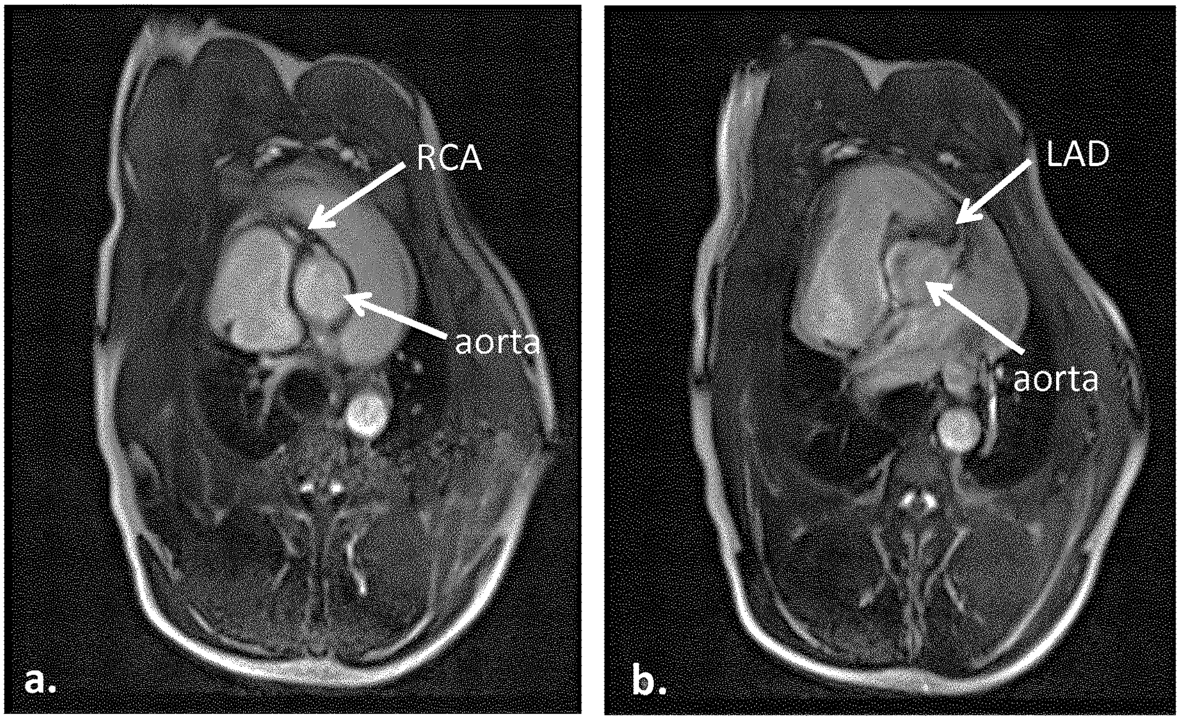
FIG. 30 shows MRI tomographic slices of (a) RCA and (b) LAD of a pig, and ((c) to (n)) time-ordered Gadolinium-based T1-weighted images of RCA (same slice location as (a)).
Figure 30:
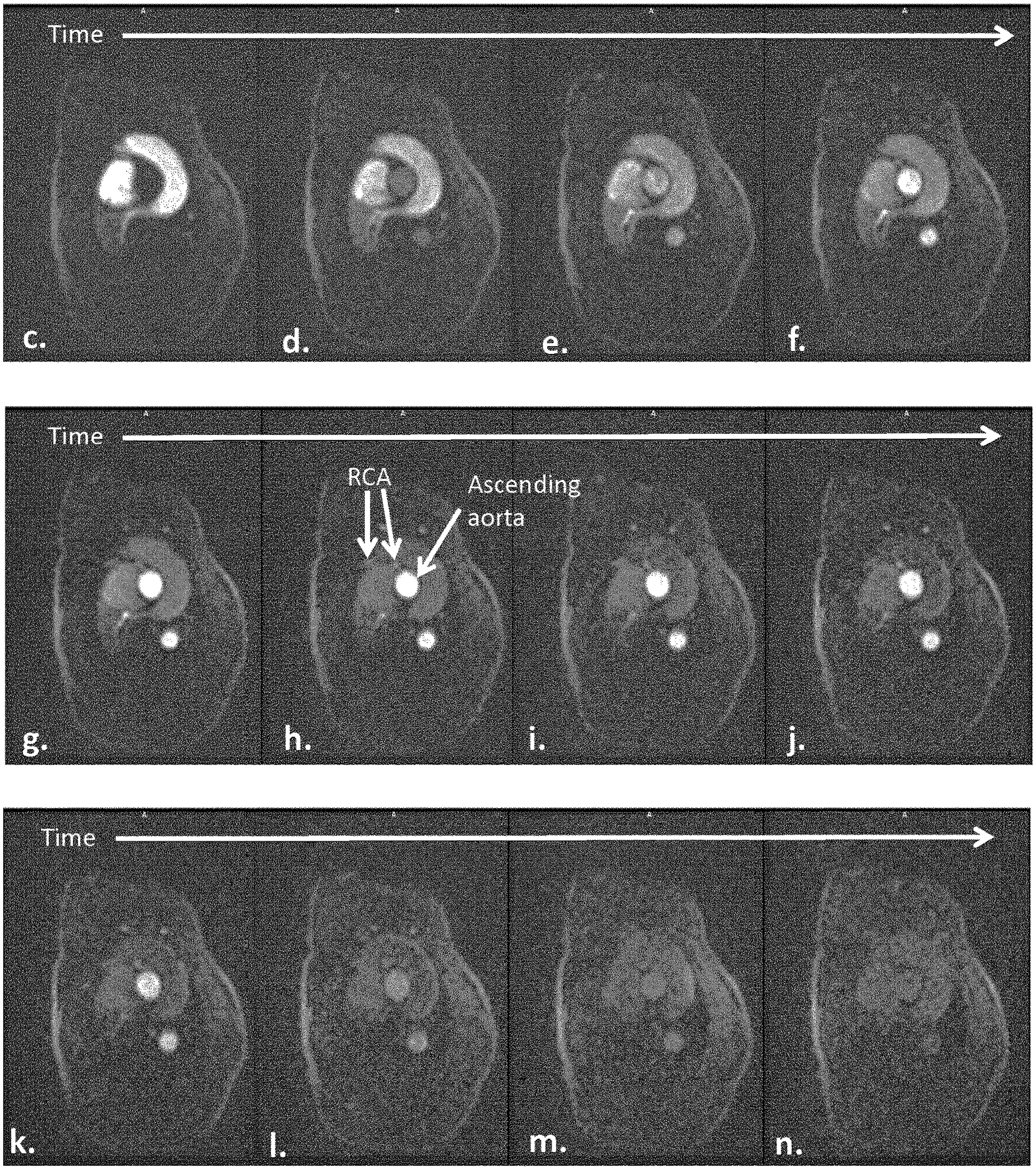

FIG. 30 shows the images acquired from a MRI study on the same pig in FIGS. 28 and 29. Images shown in FIG. 30 (*a*) and (*b*) were acquired in a supine scanning position similar to the scanning position for clinical CT and MRI studies. These images collectively illustrate that the coronary arteries such as the RCA and LAD can be seen in different tomographic slice locations in the transaxial view. The ascending aorta can also be seen in each slice for comparison.

The images displayed in FIG. 30 (*c*) to (*n*) are the T1-weighted images acquired at the same slice location as in (a) following a bolus injection of Gadolinium-based contrast agent. It is clear that the circulation of contrast in the pulmonary blood vessels can be seen at the beginning, immediately followed by the circulation of contrast in the ascending aorta and coronary arteries (RCA). The wash-out of contrast can be seen at the end of the image series. To avoid signal saturation, a low dose of contrast was used in (about 1 mmole per 20 kg body weight) at an injection rate of 2.5 mL/s followed by saline flush. The imaging was ECG triggered and one frame was acquired per heart-beat. Since the arrival of contrast changes the signal intensity in the voxels within the arteries, we can obtain coronary time-enhancement curves in a similar fashion to CT and invasive coronary angiography and provide a functional assessment as in previous Experimental Examples.

Several illustrative variants of a method or system for dynamic angiographic imaging (DAI) have been described above. Further variants and modifications are described below. Moreover, guiding relationships for configuring variants and modifications are also described below. Still further variants and modifications are contemplated and will be recognized by the person of skill in the art. It is to be understood that guiding relationships and illustrative variants or modifications are provided for the purpose of enhancing the understanding of the person of skill in the art and are not intended as limiting statements.

Figure 7:
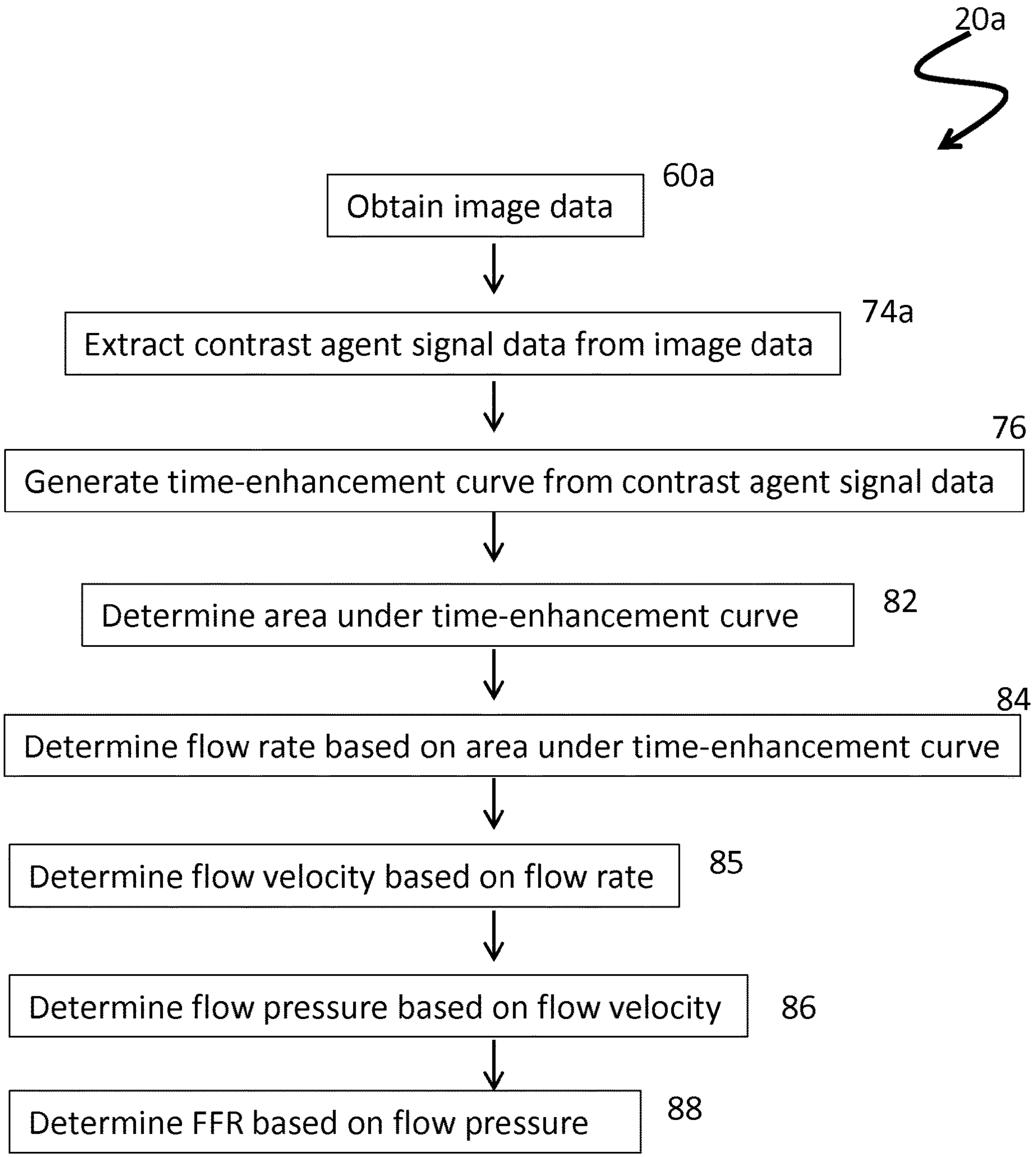
FIG. 7 shows a flow diagram of a variant DAI method.

For example, the DAI method 20 as shown FIG. 2 is merely illustrative, and should not be considered as limiting to the DAI method as one or more steps shown in FIG. 2 can be substituted or removed as desired for a specific implementation. For example, in a specific implementation CT scanning of a subject may be geographically or temporally displaced from image reconstruction. FIG. 7 shows an example, of a variant DAI method 20*a* in which both projection data from CT scanning and image reconstruction occur at a prior stage and reconstructed images are stored for analysis at either a later date or for analysis by a third party. The variant DAI method 20*a* can initiate by obtaining 60*a* the stored image data. Contrast agent signal data can then be extracted 74*a* from the stored image data, optionally without explicitly identifying a target blood vessel in the image data. A time-enhancement curve is generated 76 based on the contrast agent signal data, the time-enhancement curve having an upslope plotted from data points obtained during an increase phase of the contrast agent signal data, and a downslope plotted from data points obtained during a decline phase of the contrast agent signal data. An FFR value is then determined according to the same method steps shown in FIG. 6.

As another example, the DAI method and system are not limited to computed tomography (CT) scanning, and can readily be adapted to other imaging modalities that have sufficient spatial resolution to image blood vessels, including MRI and other X-ray imaging techniques (i.e., X-ray imaging techniques other than CT imaging), including for example fluoroscopy. X-ray based scans are a form of medical imaging comprising transmission of a high frequency electromagnetic signal that becomes attenuated as it passes through the body of a subject with the remaining signal captured by a detector for subsequent analysis. An alternative to X-ray based scans is Magnetic Resonance Imaging (MRI), which has well-recognized medical imaging applications including for example, imaging to diagnose disease in soft tissues such as the brain, lungs, liver, muscles, and heart. MRI scans involve the application of a magnetic field to a patient and the transmission of radio frequency pulses. Resonance energy is emitted by the patient and picked up by a receiver/detector that captures scan data for subsequent analysis. To improve image clarity, both X-ray scans and MRI scans involve the oral or intravenous administration of a contrast agent to a patient. Contrast agents for X-ray imaging techniques include for example iodine-based contrast agents. Contrast agent for MRI imaging techniques include for example gadolinium-based contrast agents. Scan data acquired from X-ray based scanner devices/systems are often referenced as scan data or projection data interchangeably, while scan data acquired from MRI scanner devices/systems are typically referenced as scan data. Thus, the term scan data is understood to encompass the term projection data.

Contrast agents (also referred to as tracers) for various imaging modalities are established in the current literature and continue to be an active area of development for new alternatives. The DAI method and system may accommodate any suitable combination of contrast agent and imaging modality provided that the imaging modality affords sufficient spatial resolution to image a blood vessel of interest or a portion of a blood vessel of interest.

The elapsed time of an imaging scan procedure, equivalent to the time duration of scan data acquisition, can be varied as desired provided that the imaging scan captures at least a portion of both an increase phase and a decline phase of contrast agent at the sampling site so as to obtain sufficient data to estimate shape of the time-enhancement curve. Generally, to capture both increase and decline phases an imaging scan of greater than 5 seconds is needed. In certain examples, imaging scans can be configured to capture scan data for greater than 6 seconds, greater than 7 seconds, greater than 8 seconds, greater than 9 seconds or greater than 10 seconds. Although not constrained by an upper time limit and not constrained by the transit time of contrast agent, most often imaging scans will not extend significantly beyond the expected transit time of contrast agent at a sampling site.

The number of images (also referred to as frames or individual scans) analyzed to generate the time-enhancement curve can be varied as desired provided that the number of images cumulatively captures at least a portion of both an increase phase and a decline phase of contrast agent at the sampling site so as to obtain sufficient data to estimate shape of the time-enhancement curve. Generally, to capture both increase and decline phases an imaging scans of greater than 5 images is needed. In certain examples, imaging scans can be configured to capture scan data for greater than 6 images, greater than 8 images, greater than 10 images, greater than 12 images, greater than 14 images, greater than 16 images, greater than 18 images, or greater than 20 images. Additionally, imaging scans configured to capture at least 10 images are observed to benefit consistency of peak value determinations and curve shape; signal intensity values need not be extracted from all of the at least 10 images, but the at least 10 images often provides a large enough set of images to select a subset of appropriate time-distributed images (typically 5 or more images) that leads to consistency of estimating curve shape.

The DAI method and system is considered dynamic due to analysis of a plurality of images as distinguished from static techniques that evaluate a single image. Most commercially available CT angiography techniques are static. Furthermore, commercially available CT angiography techniques that are minimally dynamic (evaluating 2 to 3 images) do not recognize or consider benefits of acquiring scan data from both the increase phase and decline phase of contrast agent transit or generating a time-enhancement curve having an upslope, peak and downslope.

A plurality of images, for example at least 5 images, for generating a time-enhancement curve are considered to be a plurality of corresponding images with the correspondence of images referring to a time-ordered sequence of multiple images located in the same sampling site or slice or in a group of adjacent sampling sites or slices (for example, consideration of adjacent sampling sites can occur in motion correction as described above for Complement Step 3 in FIG. 8). Thus, correspondence of images is spatially limited to a single sampling site or a group of adjacent sampling sites, and correspondence of images does not include sampling sites spatially separated to be upstream versus downstream of a source of blood flow aberration. For example, when determining a blood flow characteristic comprises a comparison of corresponding values calculated from first and second time-enhancement curves, the first time-enhancement curve may be generated from a first plurality (or set) of corresponding images from a first sampling site located upstream of a suspected source of a blood flow aberration and the second time-enhancement curve may be generated from a second plurality (or set) of corresponding images from a second sampling site located downstream of the suspected source of the blood flow aberration. In this example, the first set of corresponding images will not be intermingled with the second set of corresponding images as the first and second sampling sites are spatially separated by an intervening suspected source of blood flow aberration. However, as a counterpoint example, such as may occur for motion correction processing, a first set of corresponding images from a first sampling site may be intermingled in a time-specific manner (so as to maintain a time-ordered sequence in the resulting intermingled set of corresponding images) with a second set of corresponding images from a second sampling site when the first and second sampling sites (slices) are abuttingly adjacent or close to abuttingly adjacent so as to minimize blood flow differences between the first and second sampling sites.

Each set or plurality of corresponding images is time-ordered or time-resolved to generate a time-enhancement curve. The time-enhancement curve has an upslope, a peak and a downslope. Time-ordering is needed to generate the time-enhancement curve so that the upslope of the time enhancement curve is interpolated from time-specific contrast agent signal data points acquired during an increase phase of contrast agent transit, and the downslope of the time enhancement curve is interpolated from time-specific contrast agent signal data points acquired during a decline phase of contrast agent transit. Accordingly, acquisition of scan data and reconstruction of image data occurs with reference to a time-ordering scheme such that each set of corresponding images obtained from the image data can be arranged in a time-ordered sequence. A time-ordering scheme can be any convenient scheme including a time stamp with a real-time identifier, a relative-time identifier such as elapsed time from bolus injection, or any customized time identifier that can be used for identifying absolute or relative time of each image and time-resolved sequencing of the set of corresponding images. Established protocols for time intervals between contrast agent administration and image acquisition may be adopted in devising a time ordering scheme. Furthermore, established timing techniques, for example bolus tracking, may be adopted to optimize timing of scan acquisition and time-ordering of image data.

The time-enhancement curve is a plot of contrast agent signal intensity versus time derived from scan data of a contrast agent transit at a single sampling site or a group of adjacent sampling sites (e.g., for motion correction). The time-enhancement curve may also be referred to as a time-density curve, signal intensity time curve, time-dependent signal intensity, time-intensity curve among other variations. The term enhancement within the term time-enhancement curve refers to an increase in measured contrast signal intensity relative to a baseline or reference value such as signal intensity measured at a minimal level of contrast agent or measured at a residual level of contrast agent or measured in absence of contrast agent. Qualitative terms describing a contrast agent transit, such as prior to entry, entry, wash-in, increase phase, decline phase, wash-out, clearance and subsequent to clearance, are referenced to a bolus injection event or more generally a contrast agent administration event, such that each of these terms, except prior to entry, describing a portion of a contrast agent transit that occurs subsequent to an associated injection or administration event. The term prior to entry may correspond to a time range that may begin earlier than the injection or administration event.

In many examples, the DAI method and system includes generation of at least one time-enhancement curve. However, in certain examples that do not require assessment of a time-enhancement curve, for example a blood flow characteristic based on a peak enhancement value, a generation of a time-enhancement curve may not be necessary and therefore in these examples a time resolved sequencing of the set of corresponding images also becomes optional; more specifically, a set of corresponding images may be queried to identify and select an image with peak signal intensity and extract a peak enhancement value without establishing a time-enhancement curve. A risk of extracting a peak enhancement value without a time-enhancement curve is that the selected image of peak signal intensity may be an outlier that may not be apparent in absence of a comparison to a time-enhancement curve; however, this risk may be acceptable for generalized screening assessments, such as assessments of multiple sampling sites of multiple vessels in an organ in data acquired from a single scan session used as a proactive screening tool to identify blood flow aberrations. Regardless of optionality of generation of a time-enhancement curve and optionality of time-resolved sequencing, the DAI method and system requires image data comprising a plurality of corresponding images capturing at least a portion of both an increase phase and a decline phase of contrast agent transit through a blood vessel of interest.

The DAI method and system described herein allows for determination of a blood flow characteristic. A blood flow characteristic may be any metric that assesses blood flow at a region of interest in a subject. A blood flow characteristic includes, for example, flow rate, flow velocity and flow pressure. Rate, velocity, and pressure are metrics of blood flow. FFR is another metric. Shear stress is another metric. Area under the curve, rate of change of area under the curve, peak (maximum value) of the curve, and blood volume may be considered as further examples of a blood flow characteristic. Examples of calculations to determine flow rate, flow velocity, flow pressure, FFR and shear stress are provided in the Mathematical Analysis section. Benefit of determining area under the curve (AUC), rate of change of area under the curve and peak of the curve is evident from FIG. 20. FIG. 20 further shows that the time-enhancement curve itself is indicative of blood flow at a sampling site, and therefore the time-enhancement curve itself can be considered a blood flow characteristic. Further examples and comparison of additional metrics of area under curve (AUC), peak enhancement (PE), upslope, downslope, skewness, and kurtosis as derived from time-enhancement curves are illustrated in Tables 6-9.

Assessment of blood flow and determination of a blood flow characteristic can provide a diagnostic result. For example, determining time-enhancement curves at first and second sampling sites yields a first time-enhancement curve and a second time-enhancement curve; and estimating of the blood flow characteristic comprises a determination including corresponding values calculated from the first and second time-enhancement curves. The blood flow characteristic value may in itself provide a diagnostic result. In further examples, corresponding values calculated from the first and second time-enhancement curves are compared and a difference in the corresponding values beyond a predetermined threshold is indicative of a diagnostic result. Thresholds and corresponding diagnostic results can be adopted from relevant literature and medical guidelines. For example, based on current literature in FFR diagnostic analysis about 0.8 is considered normal and below 0.8 is indicative that a stenosis may have functional significance. Furthermore, with repeated use of the DAI method and system, various correlations of metrics, thresholds and diagnostic results may be developed.

A region of interest (ROI) is an area on a digital image that circumscribes or encompasses a desired anatomical location, for example a blood vessel of interest or a portion of a blood vessel of interest. Image processing systems permit extraction of data from ROI on images, including for example an average parametric value computed for all pixels within the ROI. A sampling site is the location of one or more imaging slices selected to assess a desired anatomical location, such as a blood vessel of interest. ROI may be used interchangeably with sampling site, when the sampling site is at or near the ROI. In some examples, analysis of a time-enhancement curve from a single sampling site may be sufficient to determine a blood flow characteristic or metric. In other examples, a plurality of sampling sites, or a plurality imaging slices may be analyzed to obtain a plurality of corresponding image sets and to generate a plurality of corresponding time-enhancement curves, and any number of the plurality of corresponding time-enhancement curves may be compared to determine a blood flow characteristic or blood flow metric. Conventional scanners can capture 3D image data for all or part of a blood vessel of interest, and possibly even all or parts of a plurality of blood vessels of interest. Furthermore, a scan can be subdivided into a plurality of slices as desired, and therefore interrogation of multiple sites or slices at an ROI, near an ROI, upstream of an ROI, downstream of any ROI, or any combination thereof, is feasible and convenient. In multi-slice or multi-site imaging modalities may simultaneous tomographic slices or sampling sites may be extracted per scan. Thus, the DAI method need not be limited to analysis of one or two time-enhancement curves for a scan of a contrast agent transit (entry to clearance) at blood vessel interest and a single scanning procedure with a single bolus injection of contrast agent can support a plurality of slices or sampling sites divided from the scan data as desired.

A blood vessel of interest may be any blood vessel that can be imaged by a contrast-enhanced imaging technique. The blood vessel of interest will typically have a diameter of at least about 0.1 mm, for example a diameter greater than 0.2 mm or a diameter greater than 0.3 mm. The blood vessel of interest or a designated portion of the blood vessel of interest may be identified and targeted for contrast enhanced dynamic angiographic imaging to determine a diagnosis of a blood vessel disorder or to determine a predisposition to a blood vessel disorder. The blood vessel of interest can be within any anatomical area or any organ (for example, brain, lung, heart, liver, kidney and the like) in an animal body (for example, a human body).

The DAI method is not limited to scan data acquired while a subject is in a hyperemic state (also referred to as hyperemic stress or vasodilatory stress) and time-enhancement curves generated from scan data acquired while a subject is in a non-hyperemic state (also referred to as a resting state) can produce a useful result. Examples of useful time-enhancement curves generated from scan data acquired from a subject in a resting state are shown in FIGS. 25 to 27. Inducing a hyperemic state is a well-known medical protocol in blood flow assessment and often includes administration of a vasodilator such as adenosine, sodium nitroprusside, dipyridamole, regadenoson, or nitroglycerin. Mode of administration of the vasodilator may vary depending on an imaging protocol and can include intravenous or intracoronary injection.

To determine a presence of a blood vessel disorder at a blood vessel of interest, a blood flow characteristic will be analyzed based on at least one time-enhancement curve, including for example a single time-enhancement curve generated from a scan of a single sampling site, or as another example a plurality of time-enhancement curves respectively generated from a corresponding plurality of sampling sites. In a case of stenosis a comparison of two sampling sites is beneficial to compare a blood flow characteristic determined at a sampling site upstream of the stenosis with a blood flow characteristic determined at a sampling site downstream of the stenosis. For example, FFR by definition (see Equation 9) can be considered a flow pressure ratio with a flow pressure determined downstream of stenosis as numerator and a flow pressure determined upstream of stenosis as denominator. More generally, when a blood vessel of interest is identified, a plurality of sampling sites may be designated at or near the blood vessel of interest; a time-enhancement curve generated for each of the plurality of sampling sites; a desired blood flow characteristic based on a respective time-enhancement curve determined for each of the plurality of sampling sites; and comparing the determined blood flow characteristic of each of the plurality of sampling sites to determine a blood vessel disorder. In a simplified but effective form, FIG. 20*a* shows that comparison of the time-enhancement curves generated at a plurality of sampling sites at or near the blood vessel of interest is effective to determine a presence or absence of a blood vessel disorder. Depending on a specific implementation determining of a blood flow characteristic at one or more sampling sites or determining presence of absence of a blood vessel disorder based on a comparison of blood flow characteristic at a plurality of sampling sites can provide a diagnostic result.

A blood vessel disorder (may also be referred to as a vascular disorder) assessed by the method or system described herein can be any unhealthy blood flow aberration such as a functionally significant blood flow restriction or blood flow obstruction in a cardiac or non-cardiac blood vessel that can compromise health of a subject including for example, unhealthy blood flow aberrations symptomatic of Atherosclerosis (for example, plaque formation), Carotid Artery Disease, Peripheral Artery Disease including Renal Artery Disease, Aneurysm, Raynaud's Phenomenon (Raynaud's Disease or Raynaud's Syndrome), Buerger's Disease, Peripheral Venous Disease and Varicose Veins, Thrombosis and Embolism (for example, blood clots in veins), Blood Clotting Disorders, Ischemia, Angina, Heat Attack, Stroke and Lymphedema.

The DAI method and system can be used to assess a suspected blood flow disorder, for example by providing a determination of a blood flow characteristic at a blood vessel of interest identified in a previous medical examination as possible source of an unhealthy blood flow aberration. Additionally, due in part to scan data capturing multiple blood vessels and the reduced time to process scan data, the DAI method and system may be used in a first instance to proactively assess blood flow in a specific blood vessel or specific group of blood vessels (for example, a coronary blood flow assessment) and may be implemented as a screening tool to be an initial indicator to identify a source of unhealthy blood flow aberration such as a functionally significant stenosis.

The DAI method does not require the scanned subject or patient to hold breath during a scan procedure. Breath-hold is an option in some examples. In other examples, motion correction or motion compensation processing of image data may be used for scan data acquired without breath-hold of the subject or patient.

Embodiments disclosed herein, or portions thereof, can be implemented by programming one or more computer systems or devices with computer-executable instructions embodied in a non-transitory computer-readable medium. When executed by a processor, these instructions operate to cause these computer systems and devices to perform one or more functions particular to embodiments disclosed herein. Programming techniques, computer languages, devices, and computer-readable media necessary to accomplish this are known in the art.

In an example, a non-transitory computer readable medium embodying a computer program for dynamic angiographic imaging may comprise: computer program code for obtaining image data comprising a plurality of corresponding images capturing at least a portion of both an increase phase and a decline phase of a contrast agent in a blood vessel of interest; computer program code for generating at least one time-enhancement curve of the contrast agent based on the image data, the time-enhancement curve having an upslope and a downslope; and computer program code for determining a blood flow characteristic in the blood vessel of interest based on the time-enhancement curve. In another related example, the image data comprises at least one image capturing the blood vessel of interest prior to entry of the contrast agent. In yet another related example, the computer readable medium further comprises computer program code for determining a reference value based on the at least one image capturing the blood vessel of interest prior to entry of the contrast agent, and normalizing the time-enhancement curve based on the reference value. In still another related example, the computer readable medium further comprises computer program code for acquiring scan data of the blood vessel of interest from a X-ray based scan or a MRI scan, and reconstructing image data based on the scan data.

The computer readable medium is a data storage device that can store data, which can thereafter, be read by a computer system. Examples of a computer readable medium include read-only memory, random-access memory, CD-ROMs, magnetic tape, optical data storage devices and the like. The computer readable medium may be geographically localized or may be distributed over a network coupled computer system so that the computer readable code is stored and executed in a distributed fashion.

Computer-implementation of the system or method typically comprises a memory, an interface and a processor. The types and arrangements of memory, interface and processor may be varied according to implementations. For example, the interface may include a software interface that communicates with an end-user computing device through an Internet connection. The interface may also include a physical electronic device configured to receive requests or queries from a device sending digital and/or analog information. In other examples, the interface can include a physical electronic device configured to receive signals and/or data relating to the DAI method and system, for example from an imaging scanner or image processing device.

Any suitable processor type may be used depending on a specific implementation, including for example, a microprocessor, a programmable logic controller or a field programmable logic array. Moreover, any conventional computer architecture may be used for computer-implementation of the system or method including for example a memory, a mass storage device, a processor (CPU), a Read-Only Memory (ROM), and a Random-Access Memory (RAM) generally connected to a system bus of data-processing apparatus. Memory can be implemented as a ROM, RAM, a combination thereof, or simply a general memory unit. Software modules in the form of routines and/or subroutines for carrying out features of the system or method can be stored within memory and then retrieved and processed via processor to perform a particular task or function. Similarly, one or more method steps may be encoded as a program component, stored as executable instructions within memory and then retrieved and processed via a processor. A user input device, such as a keyboard, mouse, or another pointing device, can be connected to PCI (Peripheral Component Interconnect) bus. If desired, the software may provide an environment that represents programs, files, options, and so forth by means of graphically displayed icons, menus, and dialog boxes on a computer monitor screen. For example, any number of blood flow images and blood flow characteristics may be displayed, including for example a time-enhancement curve.

Computer-implementation of the system or method may accommodate any type of end-user computing device including computing devices communicating over a networked connection. The computing device may display graphical interface elements for performing the various functions of the system or method, including for example display of a blood flow characteristic determined for a blood vessel of interest. For example, the computing device may be a server, desktop, laptop, notebook, tablet, personal digital assistant (PDA), PDA phone or smartphone, and the like. The computing device may be implemented using any appropriate combination of hardware and/or software configured for wired and/or wireless communication. Communication can occur over a network, for example, where remote control of the system is desired.

If a networked connection is desired the system or method may accommodate any type of network. The network may be a single network or a combination of multiple networks. For example, the network may include the internet and/or one or more intranets, landline networks, wireless networks, and/or other appropriate types of communication networks. In another example, the network may comprise a wireless telecommunications network (e.g., cellular phone network) adapted to communicate with other communication networks, such as the Internet. For example, the network may comprise a computer network that makes use of a TCP/IP protocol (including protocols based on TCP/IP protocol, such as HTTP, HTTPS or FTP).

Embodiments described herein are intended for illustrative purposes without any intended loss of generality. Still further variants, modifications and combinations thereof are contemplated and will be recognized by the person of skill in the art. Accordingly, the foregoing detailed description is not intended to limit scope, applicability, or configuration of claimed subject matter.

What is claimed is:

1. A computer implemented method for dynamic angiographic imaging comprising:

using a medical imaging software, obtaining CT or MRI image data comprising a plurality of corresponding images capturing at least a portion of both an increase phase and a decline phase of a contrast agent in a blood vessel of interest;

using a medical imaging software, generating at least one time-enhancement curve of the contrast agent based on the CT or MRI image data, the time-enhancement curve having an upslope and a downslope;

determining an area under the time-enhancement curve;

converting the area under the time-enhancement curve to a concentration of the contrast agent in the blood vessel of interest;

determining a blood flow characteristic in the blood vessel of interest based on a ratio of mass of the contrast agent in the blood vessel of interest and the concentration of the contrast agent in the blood vessel of interest.

2. The method of claim 1, wherein the CT or MRI image data comprises at least one image capturing the blood vessel of interest prior to entry of the contrast agent; and wherein the method further comprises determining a reference value based on the at least one image capturing the blood vessel of interest prior to the entry of the contrast agent, and normalizing the time-enhancement curve based on the reference value.

3. The method of claim 1, wherein determining the blood flow characteristic comprises determining a fractional flow reserve (FFR) value based on the ratio and using Bernoulli's equation expressed as:

$$P_A + \frac{1}{2}\rho V_A^2 + \rho g h_A = P_B + \frac{1}{2}\rho V_B^2 + \rho g h_B + P_L.$$

4. The method of claim 3, wherein FFR is determined at multiple sites within the blood vessel of interest.

5. The method of claim 1, wherein determining the blood flow characteristic comprises determining a shear stress for the blood vessel of interest based on the ratio, a radius of the blood vessel of interest, and blood viscosity.

6. The method of claim 1, further comprising acquiring scan data of the blood vessel of interest from an X-ray based CT scan or a MRI scan by scanning a subject with the contrast agent to obtain the scan data, the scan data capturing at least a portion of both the increase phase and the decline phase of the contrast agent in the blood vessel of interest, and reconstructing the CT or MRI image data based on the scan data.

7. The method of claim 1, wherein the at least one time-enhancement curve comprises a first time-enhancement curve and a second time-enhancement curve; and determining of the blood flow characteristic comprises a comparison of corresponding values calculated from the first and second time-enhancement curves.

8. The method of claim 7, wherein the first time-enhancement curve is generated from image data from a first sampling site located upstream of a suspected source of a blood flow aberration and the second time-enhancement curve is generated from image data from a second sampling site located downstream of the suspected source of the blood flow aberration.

9. The method of claim 7, wherein the first time-enhancement curve is generated from image data acquired with the blood vessel of interest in a hyperemic state and the second time-enhancement curve is generated from image data with the blood vessel of interest in a resting state, and the blood flow characteristic is a blood flow reserve determined based on a ratio of corresponding blood flow values calculated from the first and second time-enhancement curves.

10. The method of claim 1, further comprising:

selecting an image showing maximum contrast enhancement from the plurality of corresponding images;

determining a reference position of the blood vessel of interest in the selected image; and tracking the blood vessel of interest in the plurality of corresponding images based on the reference position.

11. A system for dynamic angiographic imaging comprising:

a memory for storing CT or MRI image data using a medical imaging software comprising a plurality of corresponding images capturing at least a portion of both an increase phase and a decline phase of a contrast agent in a blood vessel of interest;

a processor configured to generate using a medical imaging software at least one time-enhancement curve of the contrast agent based on the CT or MRI image data, the time-enhancement curve having an upslope and a downslope; to determine an area under the time-enhancement curve; to convert the area under the time-enhancement curve to a concentration of the contrast agent in the blood vessel of interest; and to determine a blood flow characteristic in the blood vessel of interest based on a ratio of mass of the contrast agent in the blood vessel of interest and the concentration of the contrast agent in the blood vessel of interest.

12. The system of claim 11, wherein the CT or MRI image data comprises at least one image capturing the blood vessel of interest prior to entry of the contrast agent; and wherein the processor is configured to determine a reference value based on the at least one image capturing the blood vessel of interest prior to the entry of the contrast agent, and normalize the time-enhancement curve based on the reference value.

13. The system of claim 11, wherein the blood flow characteristic is a fractional flow reserve (FFR) value determined based on the ratio and Bernoulli's equation expressed as $$P_A + \frac{1}{2}\rho V_A^2 + \rho g h_A = P_B + \frac{1}{2}\rho V_B^2 + \rho g h_B + P_L.$$

14. The system of claim 13, wherein FFR is determined at multiple sites within the blood vessel of interest.

15. The system of claim 11, wherein the blood flow characteristic is a shear stress for the blood vessel of interest determined based on the ratio, a radius of the blood vessel of interest, and blood viscosity.

16. The system of claim 11, further comprising an X-ray based CT scanner or MRI scanner configured to acquire scan data of the blood vessel of interest, the scan data capturing at least a portion of both the increase phase and the decline phase of the contrast agent in the blood vessel of interest, and reconstruct the CT or MRI image data based on the scan data.

17. The system of claim 11, wherein the at least one time-enhancement curve comprises a first time-enhancement curve and a second time-enhancement curve; and the blood flow characteristic comprises a comparison of corresponding values calculated from the first and second time-enhancement curves.

18. The system of claim 17, wherein the first time-enhancement curve is generated from image data from a first sampling site located upstream of a suspected source of a blood flow aberration and the second time-enhancement curve is generated from image data from a second sampling site located downstream of the suspected source of the blood flow aberration.

19. The system of claim 17, wherein the first time-enhancement curve is generated from image data acquired with the blood vessel of interest in a hyperemic state and the second time-enhancement curve is generated from image data with the blood vessel of interest in a resting state, and the blood flow characteristic is a blood flow reserve determined based on a ratio of corresponding blood flow values calculated from the first and second time-enhancement curves.

20. The system of claim 11, wherein the processor is configured to select an image showing maximum contrast enhancement from the plurality of corresponding images; to determine a reference position of the blood vessel of interest in the selected image; and to track the blood vessel of interest in the plurality of corresponding images based on the reference position.

21. A non-transitory computer readable medium embodying a computer program for dynamic angiographic imaging comprising:

computer program code using a medical imaging software for obtaining CT or MRI image data comprising a plurality of corresponding images capturing at least a portion of both an increase phase and a decline phase of a contrast agent in a blood vessel of interest;

computer program code using a medical imaging software for generating at least one time-enhancement curve of the contrast agent based on the CT or MRI image data, the time-enhancement curve having an upslope and a downslope;

computer program code for determining an area under the time-enhancement curve;

computer program code for converting the area under the time-enhancement curve to a concentration of the contrast agent in the blood vessel of interest;

computer program code for determining a blood flow characteristic in the blood vessel of interest based on a ratio of mass of the contrast agent in the blood vessel of interest and the concentration of the contrast agent in the blood vessel of interest.

* * * * *